US010094783B2

(12) United States Patent
Williams et al.

(10) Patent No.: US 10,094,783 B2
(45) Date of Patent: *Oct. 9, 2018

(54) PREVENTION OF CROSS-CONTAMINATION IN SYSTEMS FOR RAPID ANALYSIS OF BIOLOGICAL SAMPLES

(71) Applicant: FUNDAMENTAL SOLUTIONS CORPORATION, Easton, PA (US)

(72) Inventors: Marvin R. Williams, Easton, PA (US); Charles McBrairty, Easton, PA (US); Daniel W. Pfautz, Hatfield, PA (US); Thomas J. Zupancic, Powell, OH (US); Lingchun Zeng, Columbus, OH (US); Andrew Weiman, Langhorne, PA (US); Richard S. Brody, Columbus, OH (US); Joseph D. Kittle, Glouster, OH (US); Anthony Truscott, San Diego, CA (US); Robert Baranowski, Valley Center, CA (US)

(73) Assignee: Fundamental Solutions Corporation, Easton, PA (US)

( * ) Notice: Subject to any disclaimer, the term of this patent is extended or adjusted under 35 U.S.C. 154(b) by 173 days.

This patent is subject to a terminal disclaimer.

(21) Appl. No.: 15/215,211

(22) Filed: Jul. 20, 2016

(65) Prior Publication Data
US 2016/0327488 A1    Nov. 10, 2016

Related U.S. Application Data

(63) Continuation-in-part of application No. 14/669,970, filed on Mar. 26, 2015, now Pat. No. 9,701,994.

(Continued)

(51) Int. Cl.
*C12M 1/00* (2006.01)
*B01L 3/00* (2006.01)
(Continued)

(52) U.S. Cl.
CPC .............. *G01N 21/763* (2013.01); *B01L 3/52* (2013.01); *G01N 33/02* (2013.01); *G01N 33/536* (2013.01);
(Continued)

(58) Field of Classification Search
CPC .. G01N 21/07; G01N 21/6428; G01N 33/582; C12Q 1/70
See application file for complete search history.

(56) References Cited

U.S. PATENT DOCUMENTS

D271,335 S    11/1983   Simons
D333,992 S     3/1993   Anderson
(Continued)

FOREIGN PATENT DOCUMENTS

AU     2011250705 A1    12/2011
WO    WO 2001/001127     1/2001

OTHER PUBLICATIONS

Int'l Search Report and Written Opinion dated Feb. 27, 2013 in Intl Application No. PCT/US12/69192.
(Continued)

*Primary Examiner* — Nathan A Bowers
(74) *Attorney, Agent, or Firm* — Frost Brown Todd LLC

(57) ABSTRACT

A system for use in rapid sample analysis that includes a biosensor reagent, wherein the biosensor reagent includes living biological cells; a reservoir card, wherein the reservoir card stores the biosensor reagent; and a test cartridge base, wherein the test cartridge base is configured to accept the reservoir card, and wherein the test cartridge base further includes a reaction chamber having a central axis, wherein the reaction chamber has the shape of a revolved half ellipse; and an inlet channel connected to the reaction chamber, wherein the inlet channel is positioned above the reaction chamber at an angle of 15-60 degrees above the horizontal, (Continued)

and wherein the inlet channel is offset from the central axis of the reaction chamber.

21 Claims, 29 Drawing Sheets

Related U.S. Application Data

(60) Provisional application No. 62/195,090, filed on Jul. 21, 2015.

(51) Int. Cl.
| | | |
|---|---|---|
| *G01N 21/76* | (2006.01) | |
| *G01N 33/02* | (2006.01) | |
| *G01N 33/569* | (2006.01) | |
| *G01N 33/536* | (2006.01) | |

(52) U.S. Cl.
CPC .... *G01N 33/56916* (2013.01); *B01L 2200/16* (2013.01); *B01L 2300/047* (2013.01); *B01L 2300/0816* (2013.01); *G01N 2201/0221* (2013.01)

(56) References Cited

U.S. PATENT DOCUMENTS

| | | |
|---|---|---|
| D347,695 S | 6/1994 | Katzer et al. |
| 5,744,322 A | 4/1998 | Krejcarek et al. |
| D404,140 S | 1/1999 | Meguro |
| 6,300,138 B1 | 10/2001 | Gleason et al. |
| D462,024 S | 8/2002 | Nardo et al. |
| D559,995 S | 1/2008 | Handique et al. |
| D586,677 S | 2/2009 | Nothacker et al. |
| D608,670 S | 1/2010 | Samborn et al. |
| D610,026 S | 2/2010 | Buber |
| D633,209 S | 2/2011 | Boessneck et al. |
| D645,971 S | 9/2011 | Taylor et al. |
| D647,209 S | 10/2011 | Müller et al. |
| D668,350 S | 10/2012 | Rowley |
| D675,335 S | 1/2013 | Feuerabend et al. |
| D680,228 S | 4/2013 | Choi et al. |
| D717,459 S | 11/2014 | Lin et al. |
| 8,940,247 B2 | 1/2015 | Uehata et al. |
| 9,023,640 B2 | 5/2015 | Williams et al. |
| D731,671 S | 6/2015 | Gruner |
| D734,482 S | 7/2015 | Peterman et al. |
| D735,878 S | 8/2015 | Chang |
| D746,999 S | 1/2016 | Jonsson et al. |
| D748,814 S | 2/2016 | Han et al. |
| D759,253 S | 6/2016 | Bar-Or et al. |
| 9,551,649 B2 | 1/2017 | Houghton et al. |
| 9,645,091 B2 | 5/2017 | Slowey |
| 2001/0045355 A1 | 11/2001 | Gephart et al. |
| 2002/0123059 A1 | 9/2002 | Ho |
| 2004/0161855 A1 | 8/2004 | Kvasnik et al. |
| 2005/0118704 A1 | 6/2005 | Malobabic |
| 2006/0108218 A1 | 5/2006 | Gephart et al. |
| 2009/0136633 A1 | 5/2009 | Royds |
| 2010/0050749 A1 | 3/2010 | Yuan |
| 2010/0062415 A1 | 3/2010 | Schwoebel et al. |
| 2011/0212453 A1 | 9/2011 | Agarwal et al. |
| 2012/0190589 A1 | 7/2012 | Anderson et al. |
| 2013/0149775 A1 | 6/2013 | Williams et al. |
| 2013/0171044 A1 | 7/2013 | Nikonorov et al. |
| 2015/0346097 A1 | 12/2015 | Battrell et al. |

OTHER PUBLICATIONS

Calpe et al., "ZAP-70 enhances migration of malignant B lymphocytes toward CCL21 by inducing CCR7 expression via IgM-ERK1/2 activation", Blood, vol. 118, 16, pp. 4401-4410 (2011).

Banerjee et al, "Mammalian cell-based sensor system", Advances in Biochemical Engineering/Biotechnology, vol. 117, pp. 21-55 (2010).

Rider et al, "A B Cell-Based Sensor for Rapid Identification of Pathogens", Science, vol. 301, pp. 213-215 (Jul. 11, 2003).

Relman, "Shedding Light on Microbial Detections", New England Journal Medicine, vol. 349, No. 2, pp. 2162-2163 (Nov. 27, 2003).

Cragg et al, "Analysis of the interaction of monoclonal antibodies with surface IgM on neoplastic B-cells", British Journal of Cancer, vol. 79, No. 5/6, pp. 850-857 (1999).

Ungrin et al, "An Automated Aequorin Luminescence-Based Functional Calcium Assay for G-Protein-Coupled Receptors", Analytical Biochemistry, vol. 272, pp. 34-42 (1999).

Mead et al, "Food Related Illness and Death in the United States", Emerging Infectious Diseases, vol. 5, No. 5, pp. 607-625 (Sep.-Oct. 1999).

Banerjee et al, "Mammalian cell-based biosensors for pathogens and toxins", Trends in Biotechnology, vol. 27, No. 3, pp. 179-188 (Jan. 31, 2009).

U.S. Appl. No. 15/214,175.
Design U.S. Appl. No. 29/506,772.
Design U.S. Appl. No. 29/533,687.
Design U.S. Appl. No. 29/533,700.
Design U.S. Appl. No. 29/597,323.

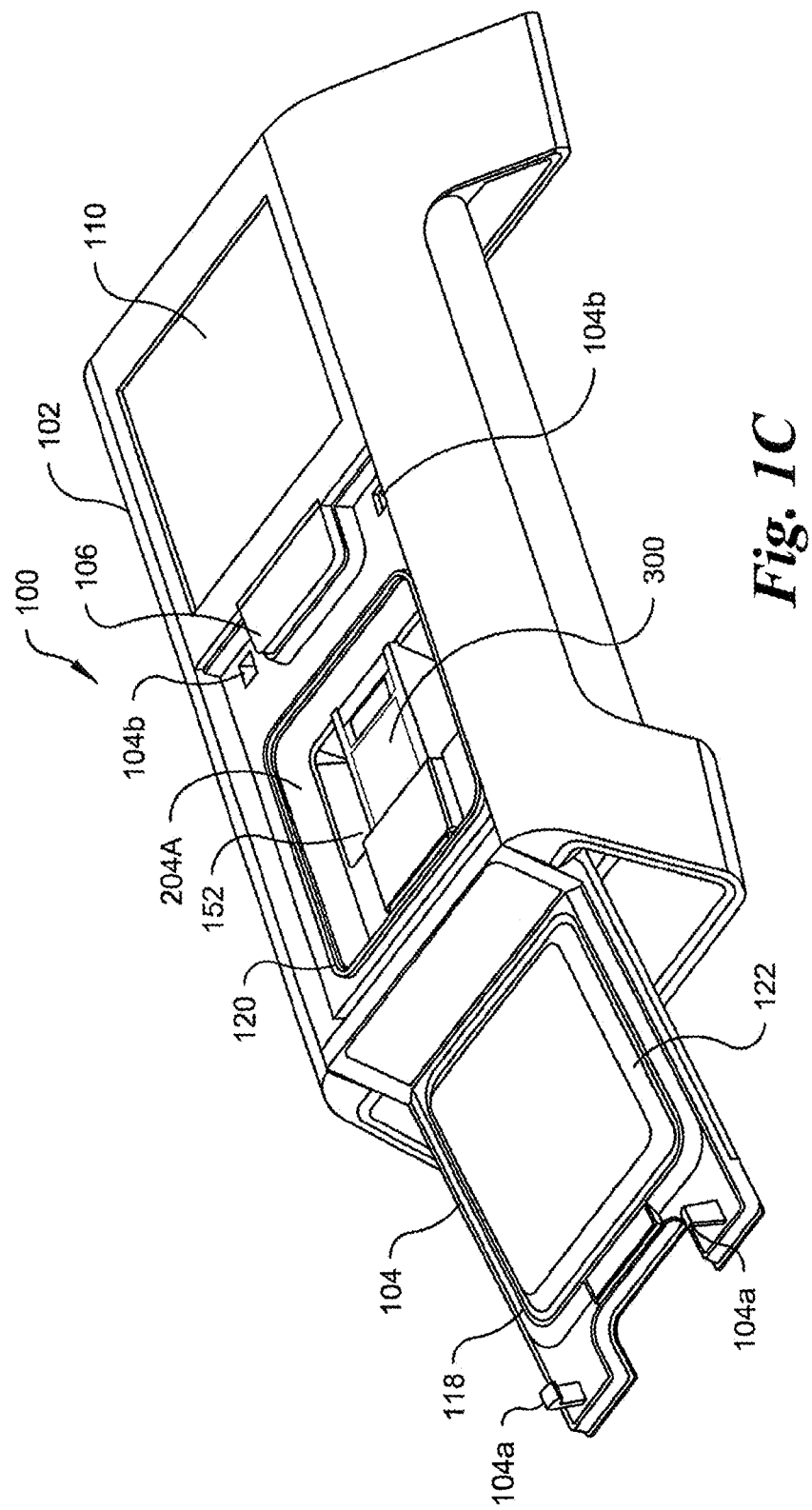

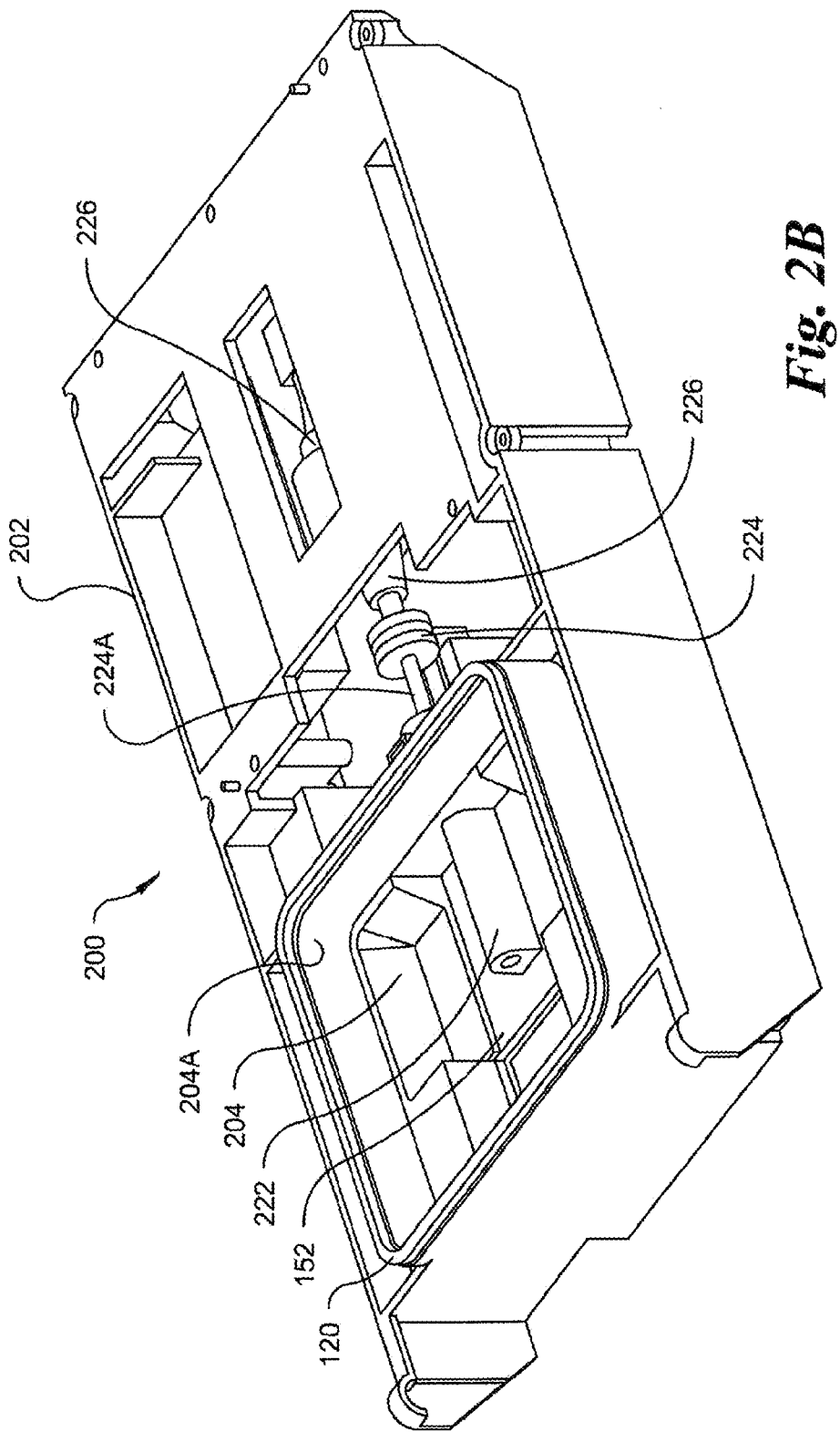

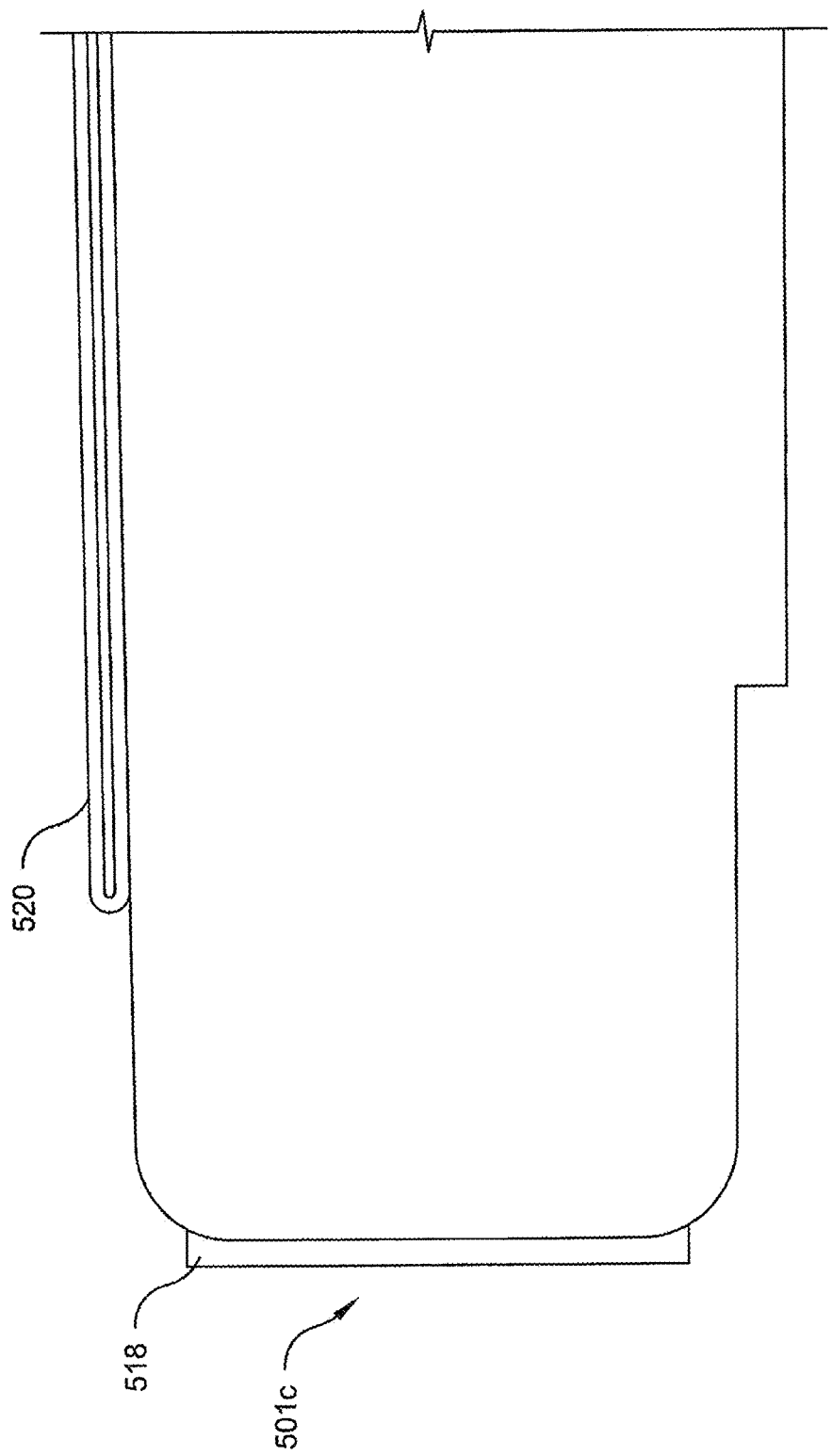

PREVENTION OF CROSS-CONTAMINATION IN SYSTEMS FOR RAPID ANALYSIS OF BIOLOGICAL SAMPLES

CROSS-REFERENCE TO RELATED APPLICATIONS

This patent application claims the benefit of U.S. Provisional Patent Application Ser. No. 62/195,090 filed on Jul. 21, 2015 and entitled "Prevention of Cross-Contamination in Systems for Rapid Analysis of Biological Samples", the disclosure of which is incorporated by reference herein in its entirety and made part of the present U.S. utility patent application for all purposes. This patent application is also a continuation-in-part of U.S. patent application Ser. No. 14/669,970 filed on Mar. 26, 2015 and entitled "System for Rapid Analysis of Biological Samples", the disclosure of which is incorporated by reference herein in its entirety and made part of the present U.S. utility patent application for all purposes.

BACKGROUND OF THE INVENTION

The described invention relates in general to a system for detecting contaminants in biological samples. More specifically, the present invention relates to a system for detecting infectious agents or pathogens in food samples in real time using a reagent such as a biosensor.

Previously, testing of samples for infectious agents was a time consuming and expensive process that was largely divorced from the manufacturing process. In order to test for the presence of an infectious agent, a sample was typically enriched or cultured. This process requires the presence of a lab, and typically, the involvement of scientists with expertise in performing the required test. Due to the need for additional culturing or enriching time, and specialized tools and skills, the testing could not easily be performed on-site during the manufacturing process. As a consequence, the manufacturing process was typically divorced from the testing process, resulting in the need for costly recalls when the testing process later found the presence of infectious agents, and the like. In other settings, such as hospitals, delays in receiving test for infectious agents can allow for the spread of such infectious agents.

Several proposals have been made to improve the speed of testing for infectious agents by using biosensors for detection. For example, application of the aequorin-Ca2+ indicator to detect *E. coli* contamination in food products was reported by Todd H. Rider et al., A B Cell-Based Sensor for Rapid Identification of Pathogens, SCIENCE, 11 Jul. 2003, pp. 213-215, the entire disclosure of which is incorporated herein by reference. However, the Rider process suffered from several drawbacks, such as a low signal-to-noise ratio that resulted in the process being undependable for use in large scale testing.

In generic terms, a biosensor is a system or device for the detection of an analyte that combines a sensitive biological component with a physicochemical detector component. The components of a typical biosensor system include a biological element, a transducer or detector element, and associated electronics or signal processors that display test results in a meaningful and useful manner. The biological element includes biological material such as tissue, microorganisms, organelles, cell receptors, enzymes, antibodies, nucleic acids, and the like that may be created by known biological engineering processes. The transducer or detector element works in a physicochemical manner (e.g., optical, piezoelectric, and/or electrochemical) that transforms a signal resulting from the interaction of the analyte with the biological element into another signal that can be more easily measured and quantified. Biosensors originated from the integration of molecular biology and information technology (e.g., microcircuits, optical fibers, etc.) to qualify or quantify biomolecule-analyte interactions such as antibody-antigen interactions.

There is demand for rapid, sensitive, easy-to-handle, and cost-effective detection tools to detect infectious agents, pathogens or/and toxins in food (see, for example, Mead et al., Food Related Illness and Death in the United States, Emerging Infectious Diseases; Vol. 5, No. 5, September-October 1999 (607-625), which is incorporated by reference herein).

Accordingly, it is desirable to provide a portable, self-contained system capable of rapidly testing samples for infectious agents in real time or near real time. It is further desirable to improve the technique of using biosensors for testing samples for infectious agents by improving the signal-to-noise ratio. It is further desirable to provide a testing device capable of being used by general staff for testing foodstuffs while in the manufacturing process.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a system for use in rapid sample analysis is provided. This system includes a biosensor reagent, wherein the biosensor reagent includes living biological cells; a reservoir card, wherein the reservoir card stores the biosensor reagent; and a test cartridge base, wherein the test cartridge base is configured to accept the reservoir card, and wherein the test cartridge base further includes a reaction chamber having a central axis, wherein the reaction chamber has the shape of a revolved half ellipse; and an inlet channel connected to the reaction chamber, wherein the inlet channel is positioned above the reaction chamber at an angle of 15-60 degrees above the horizontal, and wherein the inlet channel is offset from the central axis of the reaction chamber.

In accordance with another aspect of the present invention, a system for rapidly detecting the presence of an analyte in a biological sample is provided. This system includes a biosensor reagent; a test cartridge, and a testing unit. The biosensor reagent includes at least one antibody specific for a predetermined analyte and a bioluminescent agent, wherein the at least one antibody is expressed on the surface of living, engineered lymphocytes and wherein the bioluminescent agent is expressed by the living, engineered lymphocytes, the biosensor reagent being operative to detect the presence of a specific analyte in a sample to be tested, and emit a detectable light signal when the biosensor reagent reacts with the sample and detects the presence of the specific analyte in the sample. The test cartridge further includes a reservoir card that further includes the biosensor reagent; and a test cartridge base that is configured to accept the reservoir card and that further includes a reaction chamber having a central axis, wherein the reaction chamber has the shape of a revolved half ellipse; an inlet channel connected to the reaction chamber, wherein the inlet channel is positioned above the reaction chamber at an angle of 15-60 degrees above the horizontal, and wherein the inlet channel is offset from the central axis of the reaction chamber; and wherein upon introducing the sample into the test cartridge base through the inlet channel, the sample is homogeneously mixed with the biosensor reagent while minimizing damage to the living, engineered lymphocytes and minimizing any bubbling of the mixed biosensor reagent and sample in the reaction chamber. The testing unit further includes a sensor for detecting the detectable light signal emitted by the biosensor reagent upon reacting with the sample, the detection of the emitted detectable light signal being indicative of the presence of the analyte in the sample and, wherein detection of the specific analyte in the sample occurs in real time.

In yet another aspect of this invention, a testing device for real time detection of an analyte in a biological sample is provided. This testing device includes a housing comprising a lid and an input/output device; an analysis portion; and a control unit. The analysis portion includes a recess in the housing for accepting a disposable test cartridge containing a biological sample to be tested; an actuator for interacting with the test cartridge when the lid is closed; and a sensor associated with the recess in the housing. The test cartridge includes a reservoir card that further includes a biosensor reagent; and a test cartridge base configured to accept the reservoir card. The test cartridge base further includes a reaction chamber having a central axis, wherein the reaction chamber has the shape of a revolved half ellipse; and an inlet channel connected to the reaction chamber, wherein the inlet channel is positioned above the reaction chamber at an angle of 15-60 degrees above the horizontal and offset from the central axis of the reaction chamber. The actuator interacts with the test cartridge when the lid is closed and causes the biosensor reagent in the test cartridge to be displaced to react with the biological sample during the performance of a test, the biosensor reagent including at least one antibody specific for a predetermined analyte and a bioluminescent agent; wherein the at least one antibody is expressed on the surface of living, engineered lymphocytes and wherein the bioluminescent agent is expressed by the living, engineered lymphocytes, and wherein upon introducing the biological sample into the test cartridge base through the inlet channel, the biological sample is homogeneously mixed with the biosensor reagent while minimizing damage to the living, engineered lymphocytes and minimizing any bubbling of the mixed biosensor reagent and biological sample in the reaction chamber. The sensor associated with the recess in the housing detects a light signal emitted after the at least one biosensor reagent has been displaced by the actuator to react with the biological sample and to generate an output signal. The control unit is configured to receive an input from a user by way of the input/output device to initiate a test; in response to receiving the user input and after the biological sample has been deposited in the recess of the analysis portion, actuate the actuator to displace the biosensor reagent in the test cartridge to react with the biological sample; receive the output signal from the sensor; and output a test result to the user on the input/output device.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1C is a front perspective view of the testing device of FIGS. 1A and 1B showing a test cartridge inserted into the cartridge recess;

FIG. 2B is a front perspective view of the analysis portion of the testing device of FIG. 2A;

FIG. 6B is a magnified side view of the portion of the reservoir card in the inserted arrangement of FIG. 5C with the folded-over film retracted;

DETAILED DESCRIPTION OF THE INVENTION

Figure 1A:
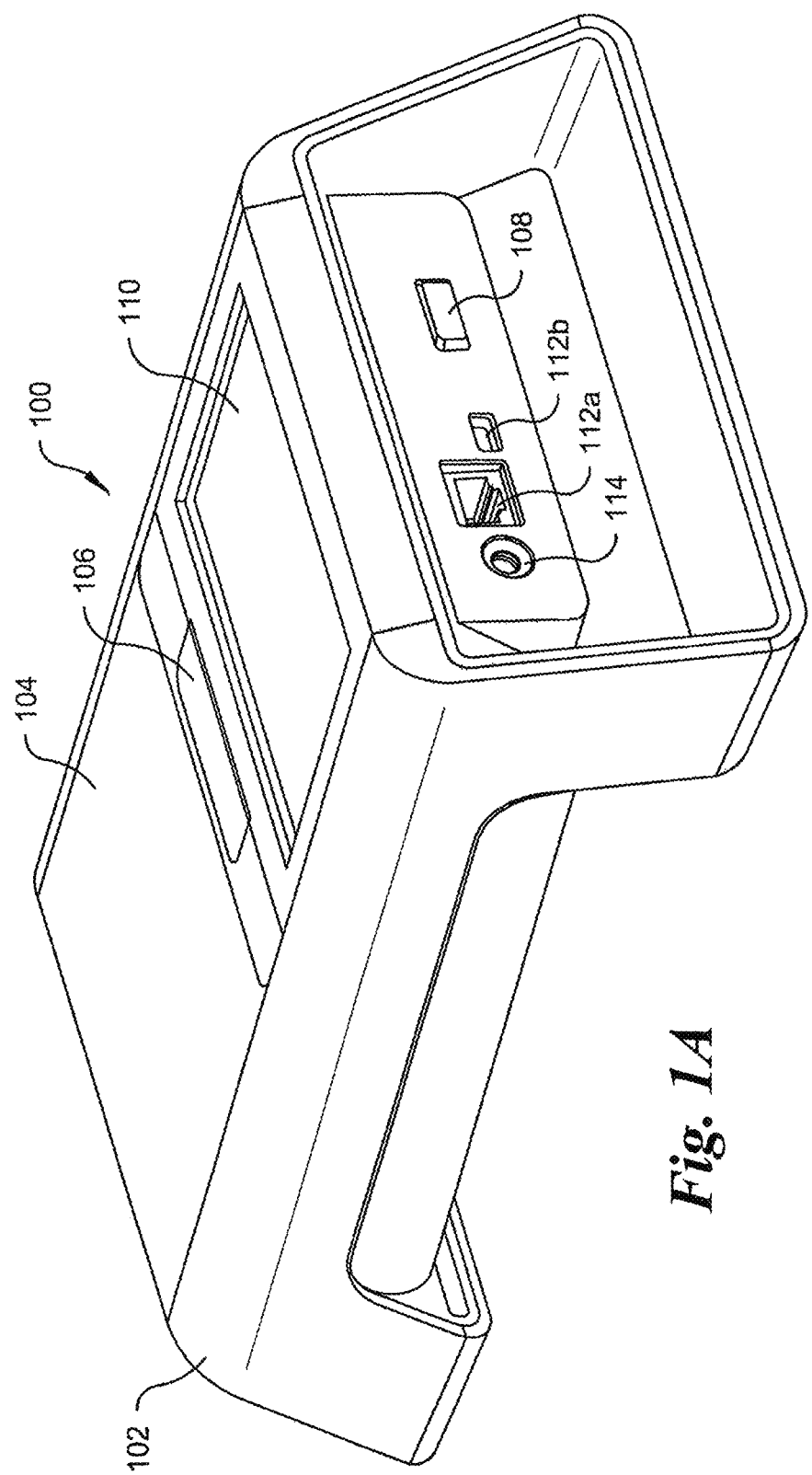
FIG. 1A is a rear perspective view of a testing device with a closed hinged lid for detecting infectious agents according to a preferred embodiment of the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the stated component and designated parts thereof. Additionally, the words "a" and "an", as used in the claims and in the corresponding portions of the specification, mean "at least one." The terminology includes the words above specifically mentioned, derivatives thereof and words of similar import.

The present invention provides a portable, self-contained system for rapidly (i.e., within one to five minutes or more) detecting infectious agents, particularly pathogens in biological samples, particularly samples derived from beef, pork, or other meat, poultry, fish, or vegetable matter, although other biological materials, such as healthcare instruments and hospital surfaces, may be analyzed using the present invention. This system provides very high sensitivity (e.g., to a single cell of a particular infectious agent) without the need to culture infectious agents, such as bacteria, obtained from samples prior to testing. In an exemplary embodiment, the specific infectious agent is *Escherichia coli*, although other infectious agents (such as *Salmonella, Listeria*, and *Campylobacter*), toxins, and various contaminants may be detected with the present invention. *Escherichia coli* O157 H7, O26, O45, O103, O111, O121, and O145, in either separate assays or multiplexed assays, may all be detected using this invention.

Figure 1B:
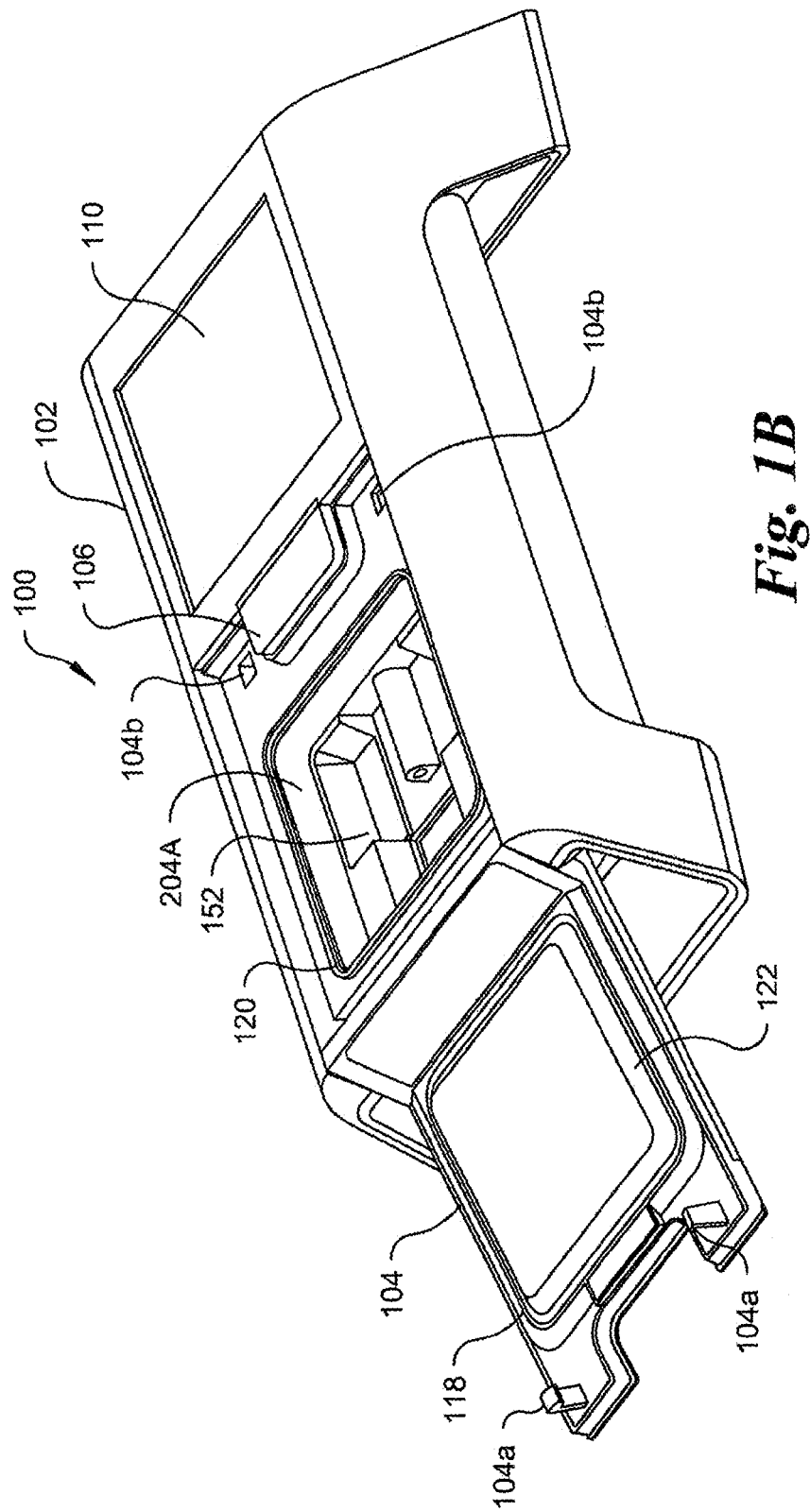
FIG. 1B is a front perspective view of the testing device of FIG. 1A with the hinged lid open to show a cartridge recess.

Referring to the drawings in detail, wherein like reference numbers refer to like elements throughout the several figures, a portable, self-contained testing device 100 for performing a variety of real-time (or near real-time) qualitative tests to rapidly detect the presence of infectious agents in biological samples such as food and other substances is shown. Referring to FIGS. 1A-1C, the testing device 100 for performing a rapid (real time or near real time) analysis of a sample 414 (FIG. 4B) to identify infectious agents according to a preferred embodiment of the present invention is shown. In a preferred embodiment, the testing device 100 utilizes a disposable test cartridge assembly 300 to test for specific analytes in a qualitative manner. The testing device 100 is a portable analyzer that interacts with the test cartridge assembly 300 and provides simple prompts for a user to obtain results for specific tests that are designed to find offending analytes from a variety of sources. The test cartridge assembly 300, which interacts with the device, contains a living biosensor, which is engineered to detect and report an offending analyte in a sample 414. Samples 414 to be tested include materials such as food, liquids, surfaces, and the like which may be sources of infectious agents. Infectious agents include food borne illnesses, pathogens, viruses, bacteria, and the like. The testing device 100 allows for rapid analysis of the sample 414 to be performed without the time-consuming need to enrich or culture the materials being tested to facilitate the test.

FIG. 1A is a front perspective view of a testing device 100 with a closed hinged lid 104 in accordance with a preferred embodiment of the present invention. The testing device 100 includes an outer housing 102 which is preferably formed of a generally rigid, preferably polymeric material, such as acrylonitrile butadiene styrene. Other materials, or combinations of materials, may be used to form the outer housing 102 without departing from the scope of this disclosure. Such materials are well known to those skilled in the art.

Figure 14:
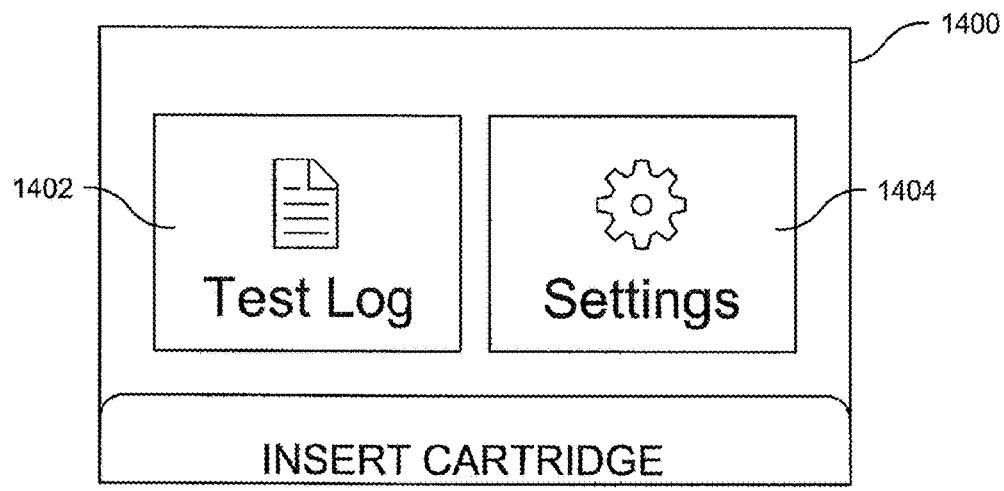
FIG. 14 is an exemplary graphical user interface of a home screen provided by the control application of FIGS. 13A and 13B.
Figure 15:
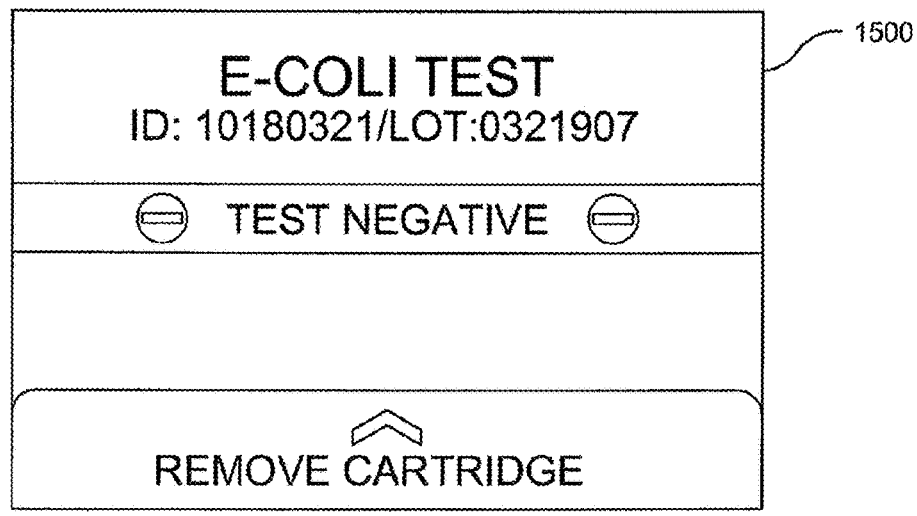
FIG. 15 is an exemplary graphical user interface showing a test result provided by the control application of FIGS. 13A and 13B.

The testing device 100 includes an ON/OFF power switch 108, and a touch screen liquid crystal display ("LCD") 110 screen for permitting a user to interact with the testing device 100 when the power switch 108 is in the ON position. The touch screen LCD 110 allows the user to provide commands to the testing device 100, and provides instructions to the user by displaying menus to facilitate operation of the testing device 100, as shown in FIGS. 14 and 15. As will be discussed further, the menus include, but are not limited to, graphical user interfaces for providing information and/or data to the user concerning the status or results of a specific test or operation being performed by the testing device 100.

In a preferred embodiment, the touch screen LCD 110 comprises an LCD unit and an overlaid touch screen capable of receiving a user's input through a latex glove, or the like. In the present embodiment, the LCD 110 comprises a five (5) inch diagonal QVGA, IPS-based TFT LCD module VL-PS-COG-T500F2080-X1 from VARITRONIX, and a glass-film-glass resistive touch screen model AD-5.0-4RU-02-200 from AD METRO. Other models and manufacturers of the touch screen LCD 110 may be utilized without departing from the scope of this invention. Furthermore, other sizes and types of input/output devices, such as buttons, keyboards, track pads, and the like, may be employed in the testing device 100 without departing from the scope of this invention.

The testing device 100 includes a plurality of interface ports 112, such as an Ethernet port 112a, and a micro USB port 112b. The interface ports 112 allow the testing device 100 to interface, download, and upload data (e.g., test data), to or from a local or remotely located computing device, mobile device, server, or the like (not shown). The structure and operation of typical interface ports 112 are well known to those skilled in the art, and are not described in detail herein for the sake of brevity. While particular interface ports 112 have been described herein, other ports and other methods of wired and/or wireless communication, such as 802.11 Wi-Fi, may be integrated and utilized in the testing device 100 without departing from the scope of this invention.

Figure 11:
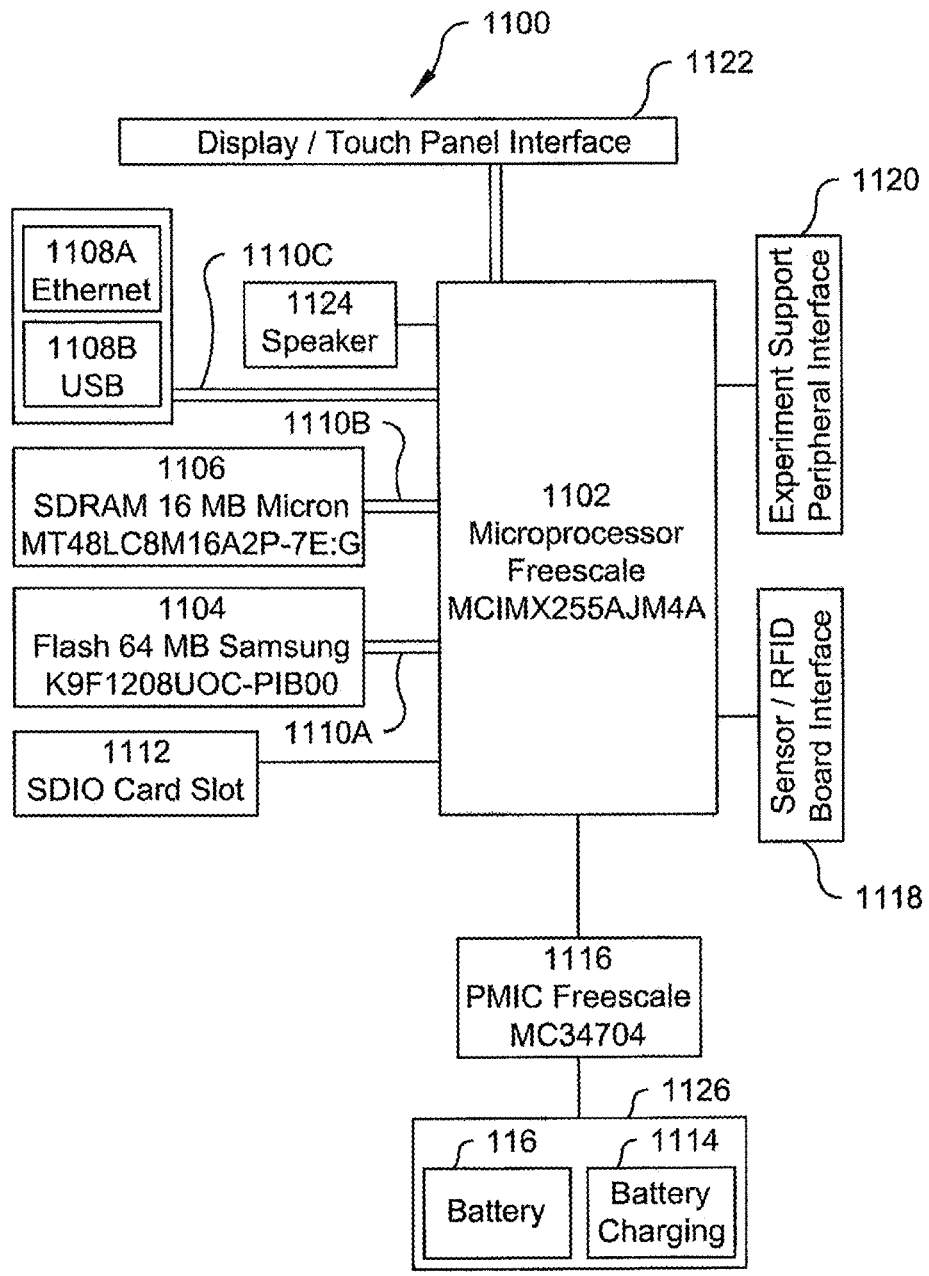
FIG. 11 is a schematic block diagram of the electrical components of the testing device of FIG. 1 according to the preferred embodiment of the present invention.

Referring to FIG. 11, the external housing 102 of the testing device 100 also contains a power supply system 1126 and other electrical and electronic components, circuitry and software necessary to permit the testing device 100 to perform testing upon an installed test cartridge assembly 300. Preferably, the power supply system 1126 comprises one or more batteries 116 to facilitate stand-alone operation of the testing device 100. A battery charger connector 114 (FIG. 1A) is also provided to charge the one or more batteries 116, which are preferably rechargeable.

The one or more batteries 116 are each preferably comprised of a double-cell lithium ion battery, model 503759AY from AUTEC BATTERY, with 2200 mAh capacity at 3.7 volts nominally. The power supply system 1126 also includes an intelligent fast charge battery charging circuit 1114 which functions to recharge the batteries 116 and monitors the battery temperature using a temperature sensor embedded within the batteries 116. In the present embodiment, the battery charging circuit 1114 is a TEXAS INSTRUMENTS model BQ240032ARHLR. If the temperature of the batteries 116 is not within safe operating range, the battery charging circuit 1114 stops the charging of the batteries 116 until a safe temperature is reached. The battery charger is activated whenever an accompanying AC adapter (not shown) is connected to the testing device 100 through the battery charger connector 114 to provide power to the testing device 100 and permit normal use of the testing device 100 during the recharging of the batteries 116.

Referring to FIG. 1B, the testing device 100 of FIG. 1A is shown with its hinged lid 104 in an open position to reveal a cartridge recess 152. The cartridge recess 152 is preferably only accessible to a user when the hinged lid 104 is in the open position. As shown in FIG. 1A, the cartridge recess 152 is covered by the hinged lid 104 when the hinged line 104 is in its closed position. The hinged lid 104 is released by a mechanical actuator 106, preferably located on the outer housing 102, proximate to the hinged lid 104. The mechanical actuator 106, which is preferably a button, switch, or the like, releases the hinged lid 104 to rotate from the closed position, which is substantially integrated with the outer housing 102 as shown in FIG. 1A, to an open position, which is away from the outer housing 102, as shown in FIG. 1B. Referring to FIG. 1C, when the hinged lid 104 is in the open position, a test cartridge assembly 300 may be introduced into the cartridge recess 152.

As shown in FIGS. 1B and 1C, the hinged lid 104 contains two lid protrusions 104a that are arranged to retain the hinged lid 104 in the closed position while a test is being performed by the testing device 100. In the closed position, the lid protrusions 104a are engaged by a pair of locking latches 104b contained within outer housing 102. The locking latches 104b are disengaged from the lid protrusions 104a by the user depressing the mechanical actuator 106. The hinged lid 104 preferably includes a light-sealing groove 118 having a light sealing gasket therein (not shown) which engages with a light sealing rib 120 in the analysis portion frame 202 (FIG. 2B) surrounding the cartridge recess 152 when the hinged lid 104 is in the closed position to prevent ambient light from entering the cartridge recess 152. A generally square projection 122 with tapered sidewalls on the interior surface of the hinged lid 104 engages with tapered sidewalls 204A of an analysis portion 200 housing 204 when the hinged lid 104 is in the closed position.

Figure 2A:
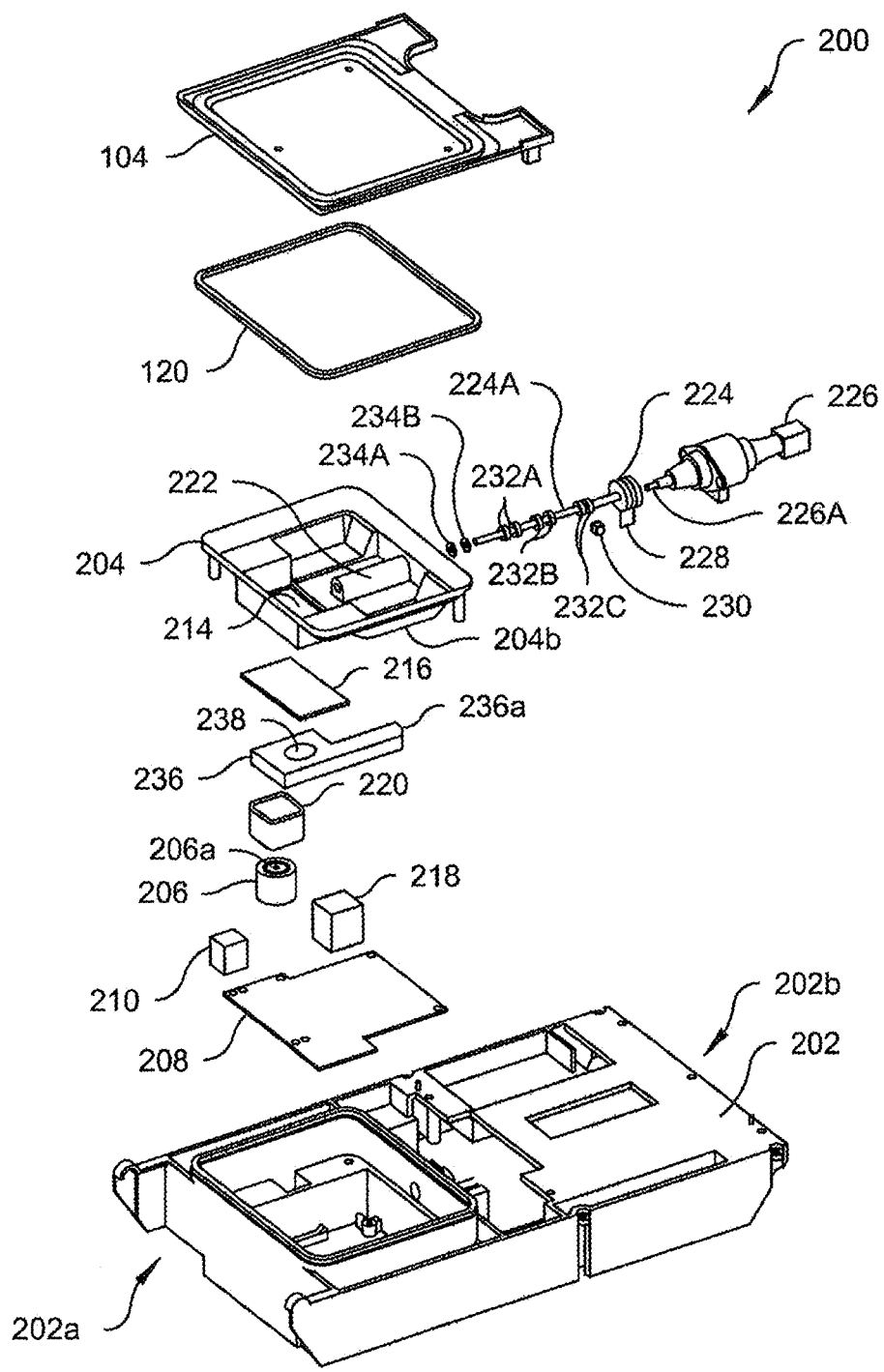
FIG. 2A is an exploded front perspective view of the components of an analysis portion of the testing device of FIG. 1 according to the preferred embodiment of the present invention.

Referring now to FIGS. 2A and 2B, an analysis portion 200 of the testing device 100 according to the preferred embodiment of this invention is shown. The analysis portion 200 includes an analysis portion frame 202 that is contained within the outer housing 102. The analysis portion frame 202 is preferably arranged in a predetermined structure and orientation, having a first end 202a and a second end 202b to facilitate acceptance of a test cartridge assembly 300 (FIG. 1C), or other compatible testing container. An analysis portion housing 204, defining the cartridge recess 152, is positioned at a first end 202a of the analysis portion frame 202. As shown in FIG. 1C, the cartridge recess 152 allows a user to introduce a test cartridge assembly 300 into the analysis portion 200 of the testing device 100 when the hinged lid 104 is in the open position. The analysis portion housing 204 functions as the interface between the testing device 100 and the test cartridge assembly 300. As will hereinafter become apparent, the disposable test cartridge assembly 300 is employed for collecting and introducing a test sample 414 (FIG. 4B) into the testing device 100 for the purpose of performing one or more tests on the test sample 414.

The analysis portion housing 204 of the analysis portion 200 will now be described in further detail. The analysis portion housing 204 is preferably made of a generally rigid, polymeric material such as acrylonitrile butadiene styrene or some other such polymeric material well known to those skilled in the art, and is located within the analysis portion frame 202. The analysis portion frame 202 provides structural support to the analysis portion housing 204, and is the main component in a light sealing scheme which greatly minimizes or prevents ambient light from entering the cartridge recess 152 by way of the rectangular walls that surround the analysis portion frame 202, thereby preventing environmental light emissions from reaching a sensor 206. In a preferred embodiment, the sensor 206 is a light sensor.

The testing device 100 performs a desired test upon a sample 414 retrieved from a variety of sources by analyzing the electrical output of the sensor 206. When the sensor 206 is a light sensor, the output varies with the amount of light incident on the sensing surface 206a of the light sensor 206 having originated within the test cartridge assembly 300. Based on the type of test being performed, the output of the light sensor 206 determines whether the analyzed sample 414 is positive or negative for the presence of the material (infectious agent) that is being sought in a qualitative analysis. That is, there need not be a determination by the testing device 100 of the actual amount of the material present in the test sample 414. The testing device 100 is capable of changing parameters for testing based on the test performed and the test cartridge assemblies 300 employed.

Since in the preferred embodiment, evaluation of the material within the test cartridge assembly 300 by the testing device 100 requires detecting the presence of light that may be emitted from the test sample 414 introduced by the test cartridge assembly 300, it is preferable to minimize or eliminate the amount of external or ambient light being introduced into the cartridge recess 152 of the testing device 100 during testing. To achieve this goal, the analysis portion 200 preferably prevents most or all environmental light emissions from reaching the sensor 206. The sensor 206 is arranged on a printed circuit board ("PCB") 208, which is positioned under the analysis portion housing 204. Minimizing such environmental light emissions from reaching the sensor 206 prevents an erroneous output from the sensor 206.

The analysis portion frame 202 and the hinged lid 104 are preferably made of a generally rigid, opaque solid material such as aluminum in order to reflect or absorb all measureable light incident on the material, or some other such opaque solid material well known to those of ordinary skill in the art. The base 204B of the analysis portion housing 204 contains a rectangular cutout 214 on a lower surface. A viewing window 216 is mounted in the rectangular cutout 214. The viewing window 216 is preferably made of an optics grade transparent solid material, such as quartz glass or another transparent solid material, as is well known to those skilled in the art. The sensor 206 is positioned beneath the viewing window 216, allowing light to pass from the test cartridge assembly 300 through the viewing window 216 to the sensor 206 with a minimal amount of light absorption or reflection. Therefore, the sensor 206 receives the maximum signal possible through the viewing window 216.

In the preferred embodiment, the sensor 206 is a light sensor, and even more preferably the sensor 206 is a photomultiplier tube (PMT), as will be described further with reference to FIG. 12. The PCB 208 further includes an RFID communications circuit 210, a high voltage power supply 218 for use with the sensor 206, and other light sensing circuitry 1200, as will be described further below with reference to FIG. 12. Preferably, the RFID communications circuit 210 is positioned beneath an area of the cartridge recess 152 that aligns with an RFID tag 508 (FIG. 5B) within the test cartridge assembly 300 when the test cartridge assembly 300 is introduced into the cartridge recess 152.

A sensor shield 220 is positioned to substantially surround the sensor 206. The sensor shield 220 isolates the sensor 206 from electromagnetic and magnetic interference. The sensor shield 220 is preferably made from a generally rigid, solid conductive material with high magnetic permeability such as mu-metal or another such solid conductive material, as is well known to those skilled in the art. One of the walls of the analysis portion housing 204 contains a hollow protrusion 222 extending into the cartridge recess 152, which mates with a recess in the test cartridge assembly 300. The hollow protrusion 222 allows a piston 224 and piston rod 224A, which engages a fluid displacement mechanism 900 (FIG. 9) in the test cartridge assembly 300, to pass therethrough and contact with a plunger 424 (FIG. 4B) of the test cartridge assembly 300.

The piston 224 is preferably made of a generally rigid, polymeric material such as polystyrene or another similar polymeric material, as is well known to those skilled in the art. The piston 224 is actuated by a motor 226. In the preferred embodiment, the motor 226 is a linear stepper motor. However, other actuators, such as pneumatic pistons, servos, or the like may be used without departing from the scope of this invention. The piston 224 is engaged to the motor 226 via a threaded shaft 226A on the motor 226 coupled to an integral threaded hole (not shown) within the piston 224. In the currently preferred embodiment, the motor 226 is a HAYDON-KERK model 19542-05-905 stepper motor. In order to reduce the introduction of noise from the motor 226 into the analysis portion 200, the motor 226 is located outside of the analysis portion housing 204, not in close proximity to the sensor 206. This arrangement of the motor 226 relative to the sensor 206 decreases the possibility of the motor 226 electrically or electromagnetically interfering with the sensor 206.

A projection 228 protrudes from the piston 224, and aligns with a position detector 230, which is positioned outside of the analysis portion 200. At a certain stage of travel of the piston 224 (described below), the projection 228 triggers the position detector 230 to generate a position signal. In one embodiment, the position detector 230 trigger position corresponds with the second position of the plunger 424 shown in FIG. 10B. However, the trigger position may alternately correspond with the final position of the plunger 424, shown in FIG. 10C, or any other position in the path of the plunger 424. In a preferred embodiment, the position detector 230 is a photo-interrupter and the position detector 230 is triggered by the projection 228 blocking the path of light within the position detector 230, at which time, a signal is sent to the microprocessor 1102 to indicate the position of the piston 224. In this way, precision sensing of the position of the piston 224 can occur to ensure that there are no errors in the actuation of the test cartridge assembly 300. In the preferred embodiment, the position detector 230 is an OMRON model EE-SX4134 photo-interrupter. However, it will be appreciated by those skilled in the art that other types of devices may be utilized for the position detector 230 without departing from the scope of this invention.

The piston 224 includes a piston rod 224A extending therefrom which contains spaced pairs of radially outwardly extending annular flanges 232A-C in spaced locations along its length. Compressible sliding seals 234A and 234B are radially mounted between the annular flanges 232A and 232C, respectively. The sliding seals 234 are preferably made of an elastomeric material such as silicone, or some other such elastomeric material, as is well known to those skilled in the art. When the piston 224 is installed, the first sliding seal 234A, mounted between annular flanges 232A engages with the interior surface of the hollow protrusion 222 of the analysis portion housing 204 to create a fluid-tight seal that prevents liquids from entering into the lower analysis portion 200, from the cartridge recess 152, and reaching the electronic components on the PCB 208 beneath the analysis portion housing 204. The second sliding seal 234B, mounted between annular flanges 232C engages with the interior surface of a hollow channel through which the piston rod 224A passes into the analysis portion frame 202 to create a light-tight seal that prevents environmental (ambient) light emissions from entering the light sealed area of the analysis portion housing 204 along the path of the piston 224.

The piston rod 224A also contains a third pair of annular flanges 232B which engage a sliding shutter 236. The sliding shutter 236 is preferably constructed of a rigid, opaque, thin material, such as a formed stainless steel sheet, for the purpose of keeping the analysis portion 200 low profile and sized to be portable. Alternately, the sliding shutter 236 may be constructed of a conductive material with high magnetic permeability, such as a mu metal in order to provide additional shielding to the sensor 206. When initially engaged by the piston rod 224A, the sliding shutter 236 passes between the sensor 206 and the viewing window 216. In this position, the sliding shutter 236 reflects or absorbs nearly all environmental light emissions that would otherwise reach the sensor 206 when the hinged lid 104 is open and the analysis portion 200 is exposed to ambient light. In the case that the sensor 206 is a PMT, the sliding shutter 236 protects the sensor 206, which is vulnerable to saturation and damage when fully exposed to ambient light levels. The sliding shutter 236 contains an aperture 238 that aligns with the sensor 206 at the start of a test. Preferably, prior to the beginning of a test, the sliding shutter 236 covers the sensor 206. It is desirable for the sliding shutter 236 to engage the piston rod 224A and make use of the motion of the motor 226 to slide into the position in which the aperture 238 is over the sensor 206 at the start of a test. This arrangement minimizes additional component costs, and further reduces the risk of electrical or electromagnetic interference.

Referring now to FIGS. 1 and 2, the analysis portion 200 is located within the housing 102 of the testing device 100. At least a portion of the analysis portion 200 is at least partially covered by the hinged lid 104 when the hinged lid 104 is in the closed position shown in FIG. 1A. The analysis portion 200 preferably includes the PCB 208 having the integral RFID communications circuit 210 that is configured to communicate via radio frequency with a unique Radio Frequency Identification ("RFID") tag 508 of a test cartridge assembly 300 (FIG. 3). In the preferred embodiment, the RFID communications circuit 210 is a TEXAS INSTRUMENTS RFID communications IC model TRF7961. However, it will be apparent to those skilled in the art that other types of scanners or scanning devices, and other data transmission schemes, could alternatively be employed for providing information to the testing device 100 and/or writing information to the RFID tag 508 of the test cartridge assembly 300.

It should be appreciated by those of ordinary skill in the art that the precise structure of the analysis portion 200 and/or its components are merely that of a currently preferred embodiment and that variations may be made to the structure of the analysis portion 200 and/or its components without departing from the scope and spirit of the invention. Thus, the present invention is not limited to the precise structure of the analysis portion 200 described herein, but is intended to encompass structural and/or operational variations, as well as other structures and arrangements which may perform the same, or substantially the same functions, as those of the current analysis portion 200.

The variations may include such structural changes as omitting an electromechanical motor, and instead relying on a user input force to actuate of the cartridge, actuating the test cartridge directly without the use of a piston, utilizing multiple motors for different actions, placing the motor within the light-sealed area of the analysis portion 200, or controlling the motor without precise position sensing. Further, the shape, arrangement and size of the test cartridge recess 152 in the analysis portion housing 204, the lid protrusions 104a, and locking latches 104b may vary from what is shown and described herein without departing from the scope of this invention. All that is necessary is that the cartridge recess 152 must compliment and conform to the size and shape of the test cartridge assembly 300 such that the cartridge recess 152 may accept an introduced test cartridge assembly 300.

Similarly, light sensing by the sensor 206 may be replaced by a different signal detection scheme, as is well known to those skilled in the art, without departing from the scope of this invention. For example, detection of electrical signals could be employed for evaluation of the test result. In this case, it may be preferable to minimize or eliminate extraneous sources of noise other than light. Structural changes to the analysis portion 200 that facilitate the minimizing or eliminating such extraneous sources of noise other than light are within the scope of this invention.

Figure 3A:
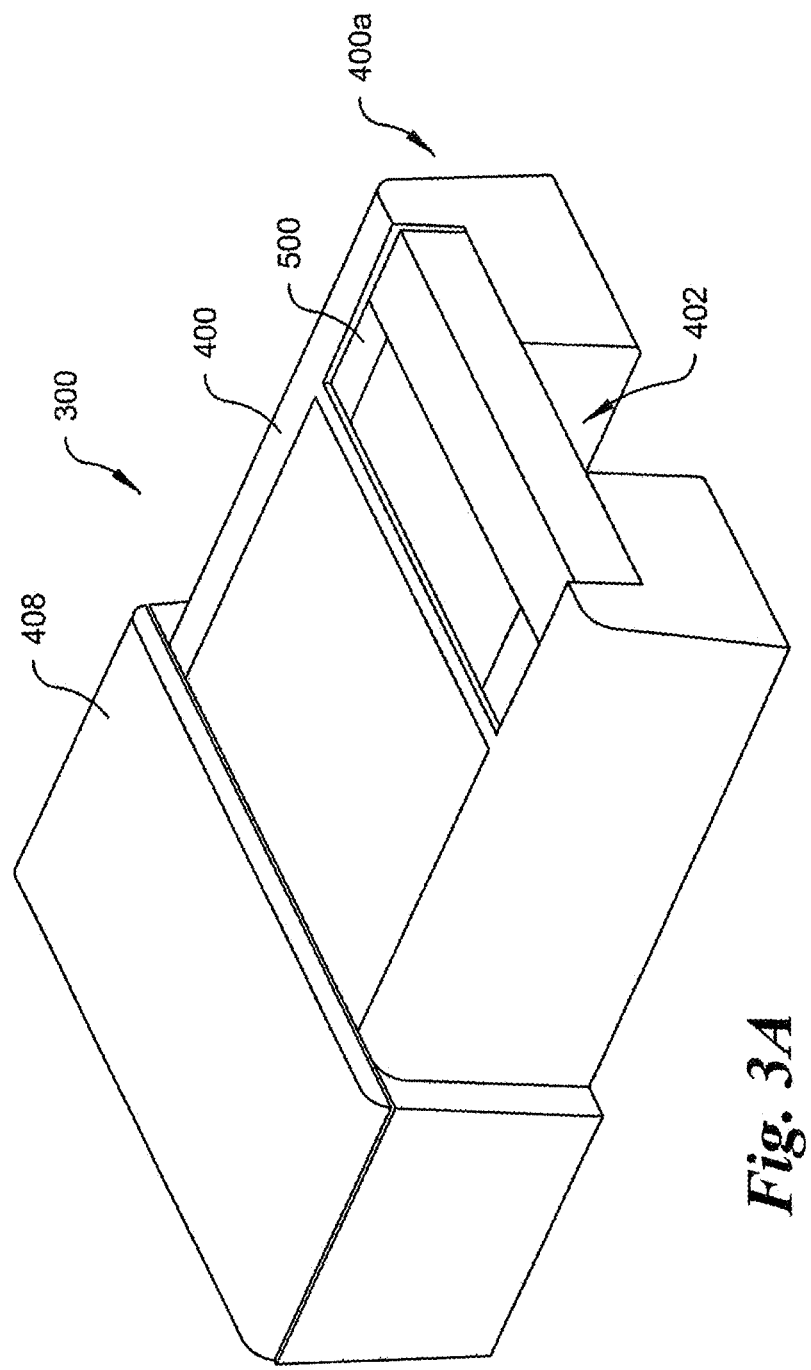
FIG. 3A is a front perspective view of a test cartridge assembly comprising a reservoir card inserted into a test cartridge base with a base lid closed for use with the testing device of FIG. 1 according to the preferred embodiment of the present invention.
Figure 3B:
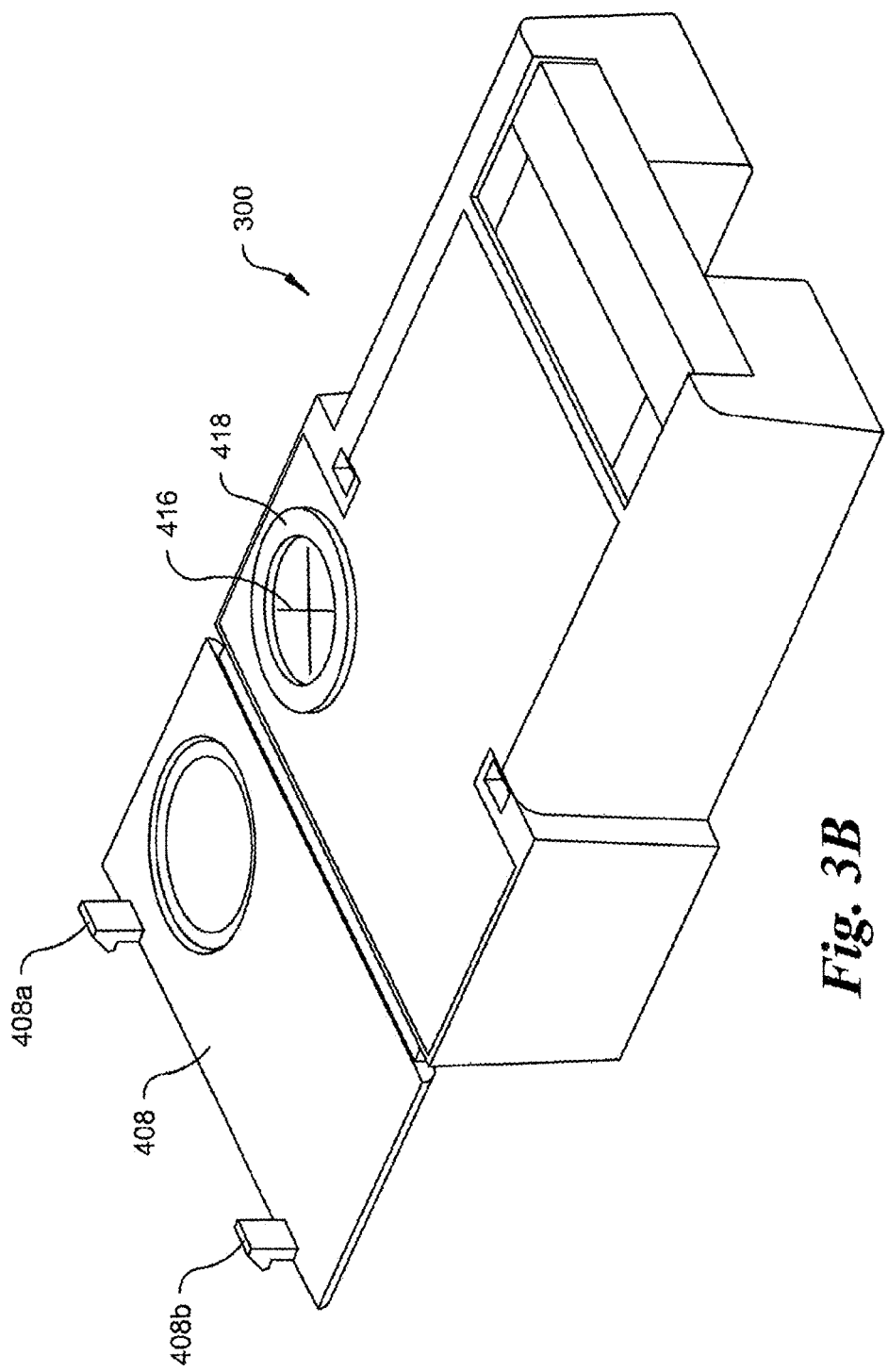
FIG. 3B is a front perspective view of the test cartridge assembly of FIG. 3A with the test cartridge base lid open.

Referring now to FIGS. 3A and 3B, there is shown the test cartridge assembly 300 for use with the testing device 100 according to the preferred embodiment of the present invention. Preferably, the test cartridge assembly 300 is a single-use, disposable cartridge that is employed for receiving a small quantity of a sample 414 (FIG. 4B) gathered from foodstuffs or other sources for a test to be performed by the testing device 100. Therefore, the test cartridge assembly 300 is preferably configured to be fixedly insertable into the testing device 100 for the duration of a performance of a selected test. Even more preferably, each test cartridge assembly 300 contains all the necessary reagents 504, 506 (FIG. 5B) and the like for the performance of a single test, as will be described further herein.

As shown in FIG. 3A, the test cartridge assembly 300 preferably comprises two separate portions, a test cartridge base 400, described further with reference to FIG. 4, and a reservoir card 500, described further with reference to FIG. 5. The test cartridge base 400 and the reservoir card 500 are configured to interact with one another for the performance of a test by the testing device 100. The reservoir card 500 is designed as a separate part from the test cartridge base 400 in order to occupy a minimal volume, and to achieve a high packing density. Packing density is a critical consideration for the occasions when the necessary reagents 504, 506 require storage at low or below freezing temperatures. However, an integrated, single unit, test cartridge assembly 300 may similarly be produced, and is within the scope of this disclosure.

Figure 4A:
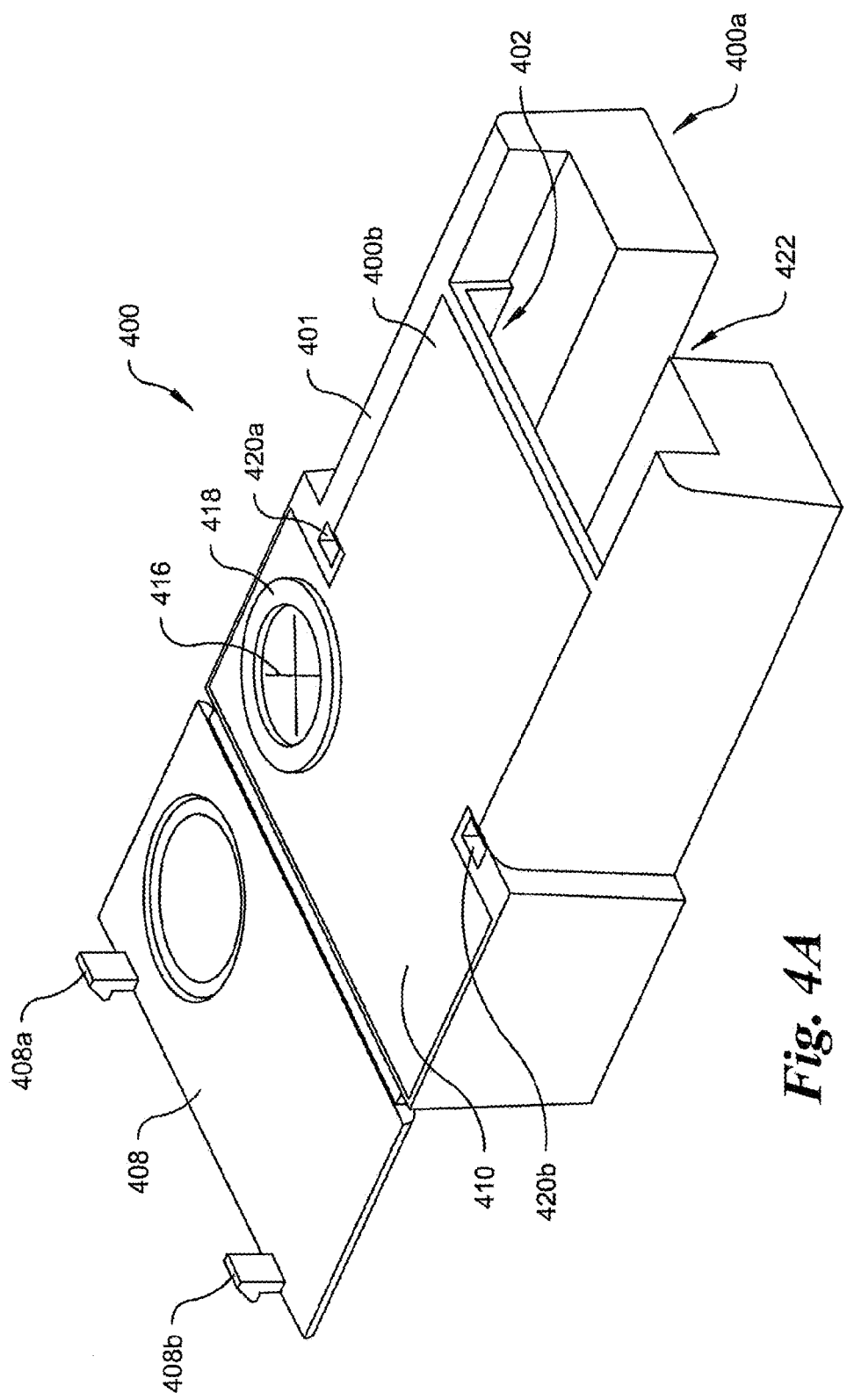
FIG. 4A is a front perspective view of the test cartridge base with the base lid open of the test cartridge assembly of FIG. 3B according to the preferred embodiment of the present invention.
Figure 5A:
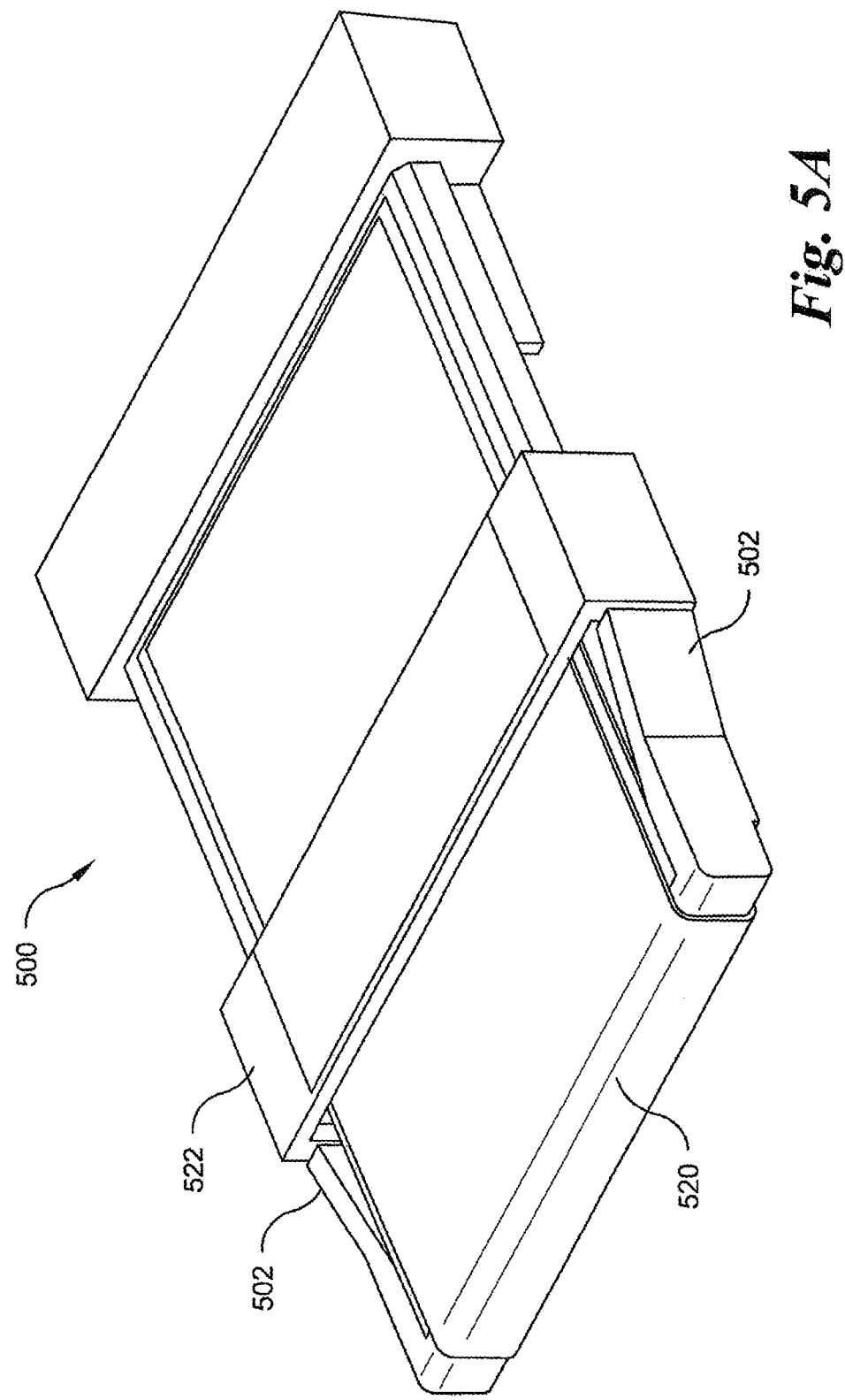
FIG. 5A is a front perspective view of the reservoir card in an initial arrangement for use in the test cartridge assembly of FIG. 3A according to the preferred embodiment of the present invention.
Figure 5B:
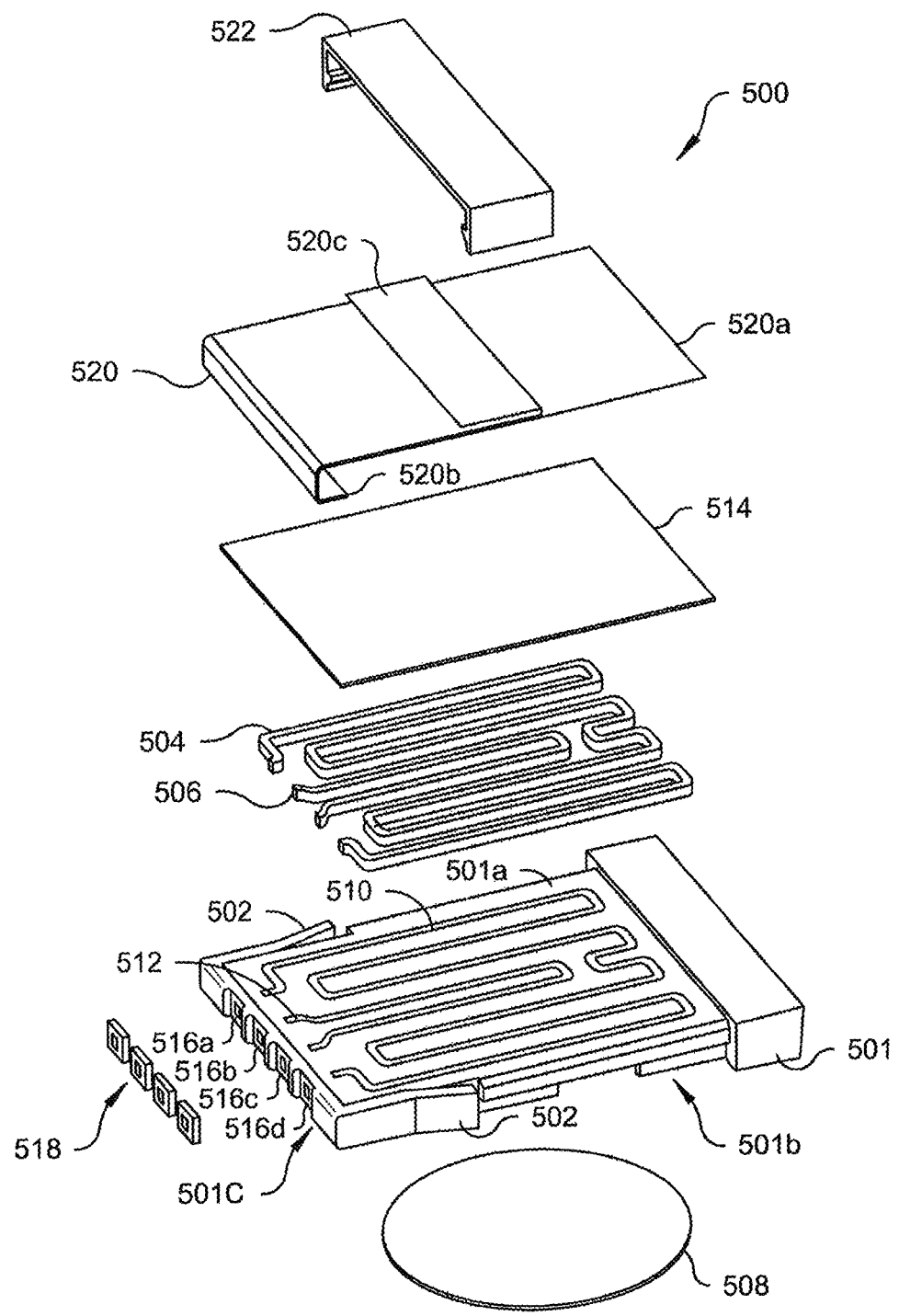
FIG. 5B is an exploded front perspective view of the components of the reservoir card of FIG. 5A.

The test cartridge base 400 is configured to accept the separate reservoir card 500 in a slot 402 (FIG. 4A) at a first end 400a of the test cartridge base 400. The reservoir card 500 is specifically designed to provide a convenient, small sized storage and delivery vehicle for one or more biosensors (reagents 504, 506). As shown in FIGS. 3A and 3B, a user assembles the reservoir card 500 into the test cartridge base 400 by sliding the reservoir card 500 into the slot 402. Once the reservoir card 500 is inserted into the test cartridge base 400, the reservoir card 500 is fixedly attached to the test cartridge base 400. The permanent attachment features 502 prevent misuse of the test cartridge base 400, such as reuse of the test cartridge base 400 with multiple reservoir cards 500. Contamination of the test cartridge base 400 and/or reservoir card 500 is thereby avoided. The reservoir card 500 may be attached to the test cartridge base 400 using any known suitable mechanical attachment device or member, such as the one way attachment features 502 (FIG. 5B).

Figure 4B:
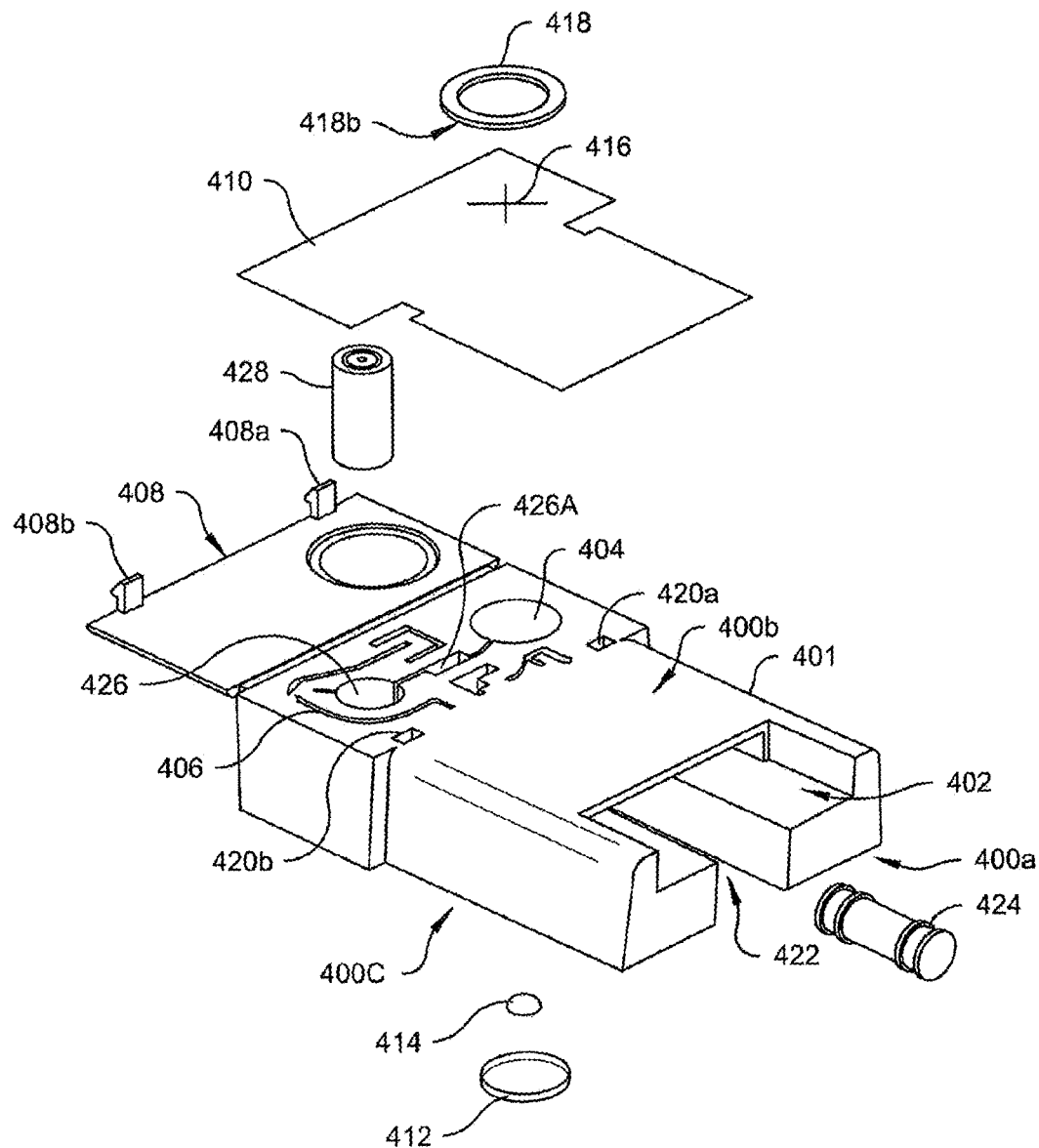
FIG. 4B is an exploded front perspective view of the components of the test cartridge base of FIG. 4A.
Figure 9:
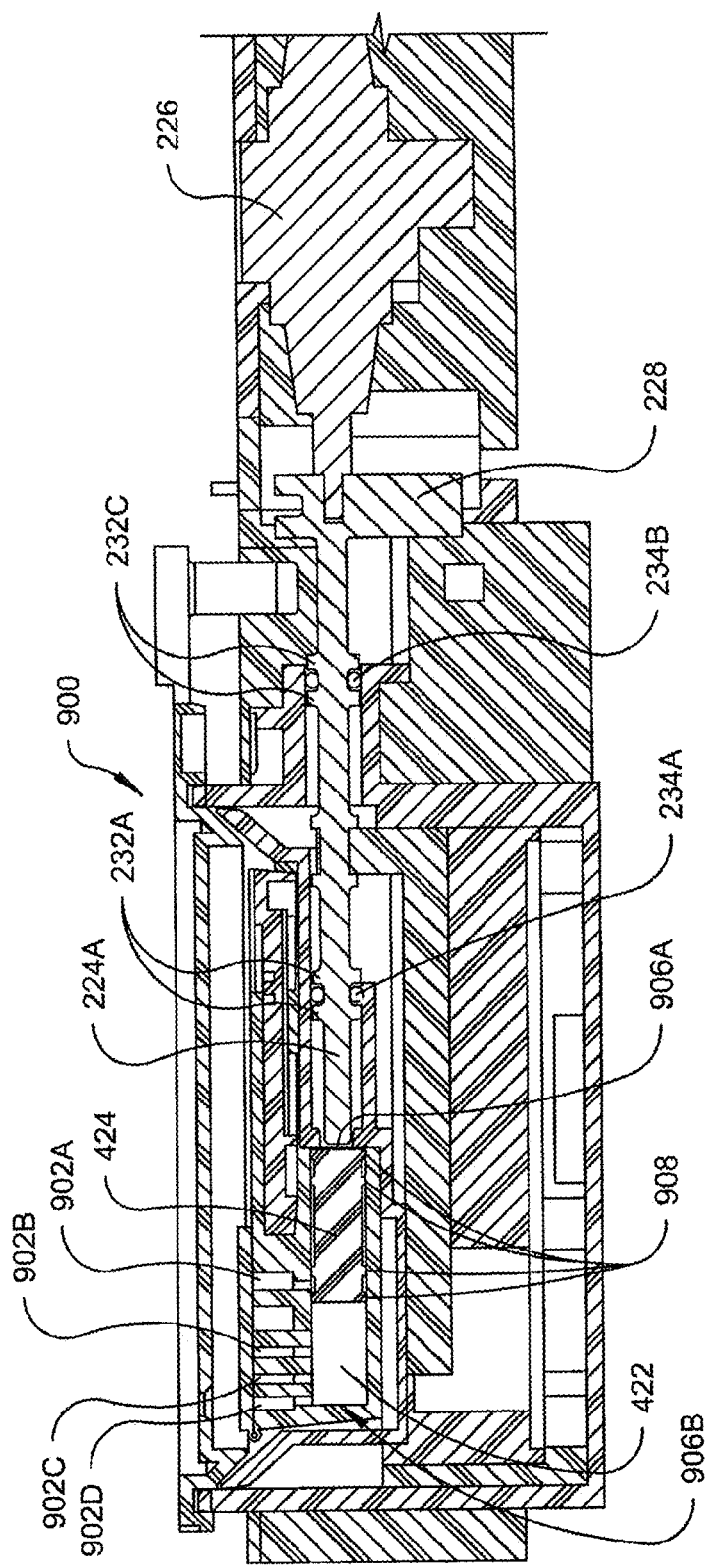
FIG. 9 is a cross-sectional side view of the test cartridge assembly of FIG. 3A inserted into the analysis portion of the testing device of FIG. 2B.

The test cartridge base 400 preferably does not contain any test-specialized components, and may therefore be common to a plurality of test types. As such, the test cartridge base 400 should be compatible with multiple types of reservoir cards 500. As shown in FIGS. 4B and 9, the test cartridge base 400 contains a reaction chamber 404 and a fluid displacement mechanism 900, which together occupy a relatively large volume in comparison to the volume of the reservoir card 500. Referring to FIGS. 5A and 5B, the reservoir card 500 contains all of the necessary reagents 504, 506, and the like, for performing a single test by the testing device 100. Accordingly, a plurality of distinct types of reservoir cards 500, each having one or more distinct reagents 504, 506 for performing a particular test type, may be provided. Preferably, the reaction chamber 404 facilitates a proper mixture of the sample 414 and the reagents 504, 506, while minimizing damage to the living cells which comprise the reagents 504, 506. The reaction chamber 404 also maximizes gathering the light that the reagents 504, 506 emits to the sensor 206 in the presence of an offensive analyte or to confirm the proper functioning of the first phase of the test.

As best shown in FIG. 4B, the test cartridge base 400 is comprised of a generally rectangular housing 401 with an integral hinged lid 408. The rectangular housing 401 is preferably formed of a generally rigid, preferably polymeric material, such as polypropylene or another such polymeric material well-known to those skilled in the art. An adhesive-backed film 410 is used to enclose fluid channels 406 formed in the planar surface 400b of the housing 401 for the sealed passage of reagents 504, 506 and/or air between the reservoir card 500 and the test cartridge base 400. The test cartridge base 400 housing 401 also includes an integral reaction chamber 404 for deposition of the sample 414, and eventual mixing of the sample 414 with the reagents 504, 506 for performing the desired test.

Figure 3C:
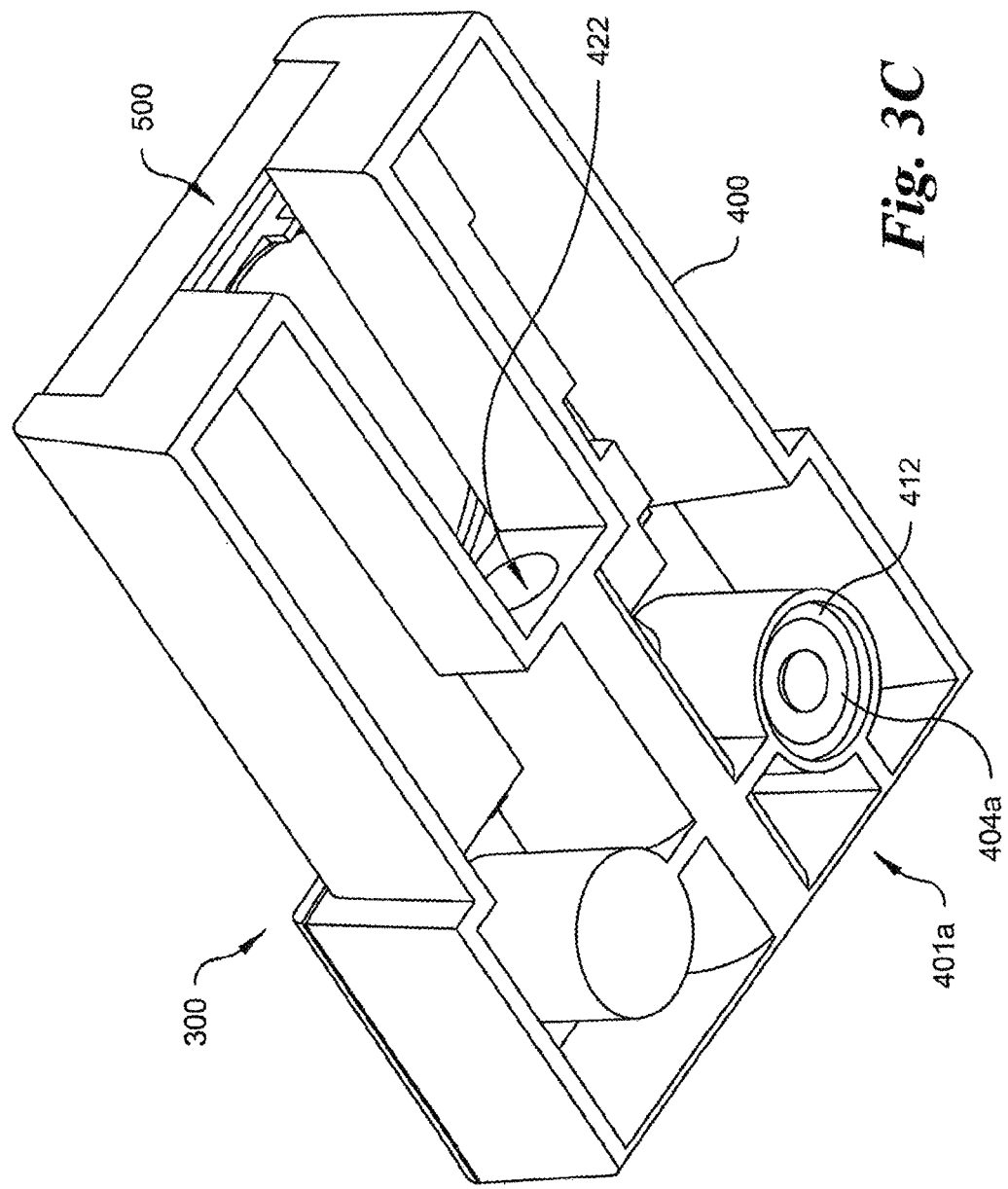
FIG. 3C is a bottom perspective view of the test cartridge assembly of FIGS. 3A and 3B.

When the test cartridge assembly 300 is placed in the cartridge recess 152, the bottom surface 404a of the reaction chamber 404 within the test cartridge base 400 housing 401 is aligned with the light sensor 206. Referring to FIG. 3C, the reaction chamber 404 is sealed on the bottom surface with a lens 412. The lens 412 is preferably formed of a rigid, preferably polymeric material such as polycarbonate or some other such polymeric material well-known to those skilled in the art. The lens 412 material is preferably an optics grade transparent material in order to prevent unwanted light absorption or reflection between the reagents 504, 506 and the light sensor 206. In the preferred embodiment, the lens 412 is thermally welded to the test cartridge base 400 housing 401 in order to provide a liquid-tight seal and minimize the introduction of contaminants into the reaction chamber 404. Referring to FIGS. 4A and 4B, the reaction chamber 404 is open to the top surface 400b of the test cartridge base 400 housing 401 in order to allow a user to directly deposit the sample 414 (preferably in liquid form) into the reaction chamber 404.

The adhesive-backed film 410 is placed on the top surface 400b of the test cartridge base 400 housing 401. The film 410 is preferably pre-scored or perforated 416 above the reaction chamber 404 in a way that allows the user to pierce through the film 410 using the tip of a deposition tool (not shown), such as a pipette for deposition of the sample 414 into the reaction chamber 404. The pre-scoring or perforation 416 of the film 410 is desirable in order to provide a visual cue to the user that they have completed the sample deposition step in the test process, or that the test cartridge assembly 300 was previously used and should be discarded. A compressible gasket 418 with adhesive backing 418b is placed around the perimeter of the opening on the top surface 400b to the reaction chamber 404 (surrounding the perforated or pre-scored area 416 of the adhesive backed film 410, see FIG. 4A) for the purpose of creating a fluid-tight seal when the integral test cartridge base 400 hinged lid 408 is closed. The integral test cartridge base 400 hinged lid 408 contains snap features 408a, 408b to retain the test cartridge base 400 hinged lid 408 in a closed position by interacting with catch slots 420a, 420b after the sample 414 has been deposited into the reaction chamber 404.

Still referring to FIGS. 4B and 3C, a central bore 422 is located within the test cartridge base 400 housing 401 that contains a plunger 424 as part of the test cartridge's fluid displacement mechanism 900, which will hereinafter be described in greater detail. The plunger 424 is preferably made of an elastomeric material, such as silicone rubber or some other such elastomeric material, as is well-known to those skilled in the art and is sized to sealingly engage the interior wall of the central bore 422. The top surface 400b of the test cartridge base 400 housing 401 contains a relatively large vent overflow chamber 426 which communicates with the reaction chamber 404 by a vent channel 426A. The vent overflow chamber 426 is present to allow air to be displaced out of the reaction chamber 404 during the introduction of the reagents 504, 506, and contains features to contain any stray amount of liquid that may enter the vent channel 426A. Preferably, the vent overflow chamber 426 contains an absorbent material 428 utilizing an anti-microbial coating that the vented air must pass through as it exits the test cartridge base 400 housing 401. This ensures that any stray amount of liquid will be absorbed and contained within the vent overflow chamber 426, and any biological components will be destroyed.

As shown in FIG. 5B, the reservoir card 500 includes a plurality of fluid ports 516, which when the reservoir card 500 is inserted into the test cartridge base 400 housing 401 interface with a series of sealing features 702 (FIG. 7), thereby making connections with the reservoir card 500 when assembled. The sealing features 702 are recessed under a wall 401A (FIG. 7) in the test cartridge base 400 housing 401 for the purpose of preventing damage to the sealing features 702, and eliminating potential sites for easily contacted contaminants to be introduced to the reagents 504, 506. FIGS. 5D, 5E, and 5F illustrate alternate embodiments that include various structures and components for preventing cross-contamination within the reservoir card. In the embodiment shown in FIG. 5D, a protective film 517 is manually removed by the user to uncover fluid ports 516 before inserting reservoir card 500 into test cartridge base 400. Positive control test features designed into the testing device detect faulty cartridge operation if the film is not removed, thereby preventing erroneous test results due to user error. With reference to FIG. 5E, an alternative to a protective film is to recess fluid ports 516 on reservoir card 500 and fluid ports 419 on cartridge base 400 so they cannot be accessed by the user and cross contaminated with other fluids. An outer bag or wrapper may be included for preventing dust or other debris from contaminating the areas that contact one another. With reference to FIG. 5F, an alternative to a protective film is recessing fluid ports 516 on reservoir card 500 and fluid ports 419 on cartridge base 400 so these structures cannot be accessed by the user and cross contaminated with other fluid samples. In this embodiment, reservoir card 500 is sealed with pierceable membrane 519 and cartridge base 400 includes a sharp needle-like feature 417 for piercing, self-sealing, and delivering fluids to mixing/reaction chamber 404. These features are typically recessed to prevent accidental injury or surface contamination by the user.

It should be appreciated by those skilled in the art that the precise structure of the test cartridge base 400 and/or its components are merely that of a preferred embodiment, and that variations may be made to the structure of the test cartridge base 400 and/or its components without departing from the scope and spirit of the invention. Other structural and functional variations, such as, depositing the sample 414 in a location other than the reaction chamber 404 to be moved to the reaction chamber 404 at a later time, utilizing multiple parts to achieve the test cartridge base 400 housing 401, and reaction chamber 404 features, using a separate lid or closure scheme for the reaction chamber 404 after sample deposition, or alternatively locating the plunger 424 and/or other components of the fluid displacement mechanism 900 on the reservoir card 500 are all within the scope of this invention.

The reaction chamber 404 and fluid channels 406 that lead to the reaction chamber 404 within the test cartridge base 400 housing 401 are preferably designed to achieve several objectives. An inlet channel 802 (FIG. 8) for fluid entering the reaction chamber 404 is preferably tubular in shape with a diameter which is preferably small and tapers to become smaller at the inlet to the reaction chamber 404. This structure preferably increases the velocity of fluids entering the reaction chamber 404 to promote vigorous, and therefore homogenous, mixing due to the bulk motion of the of the reagents 504, 506 within the reaction chamber 404.

Figure 8:
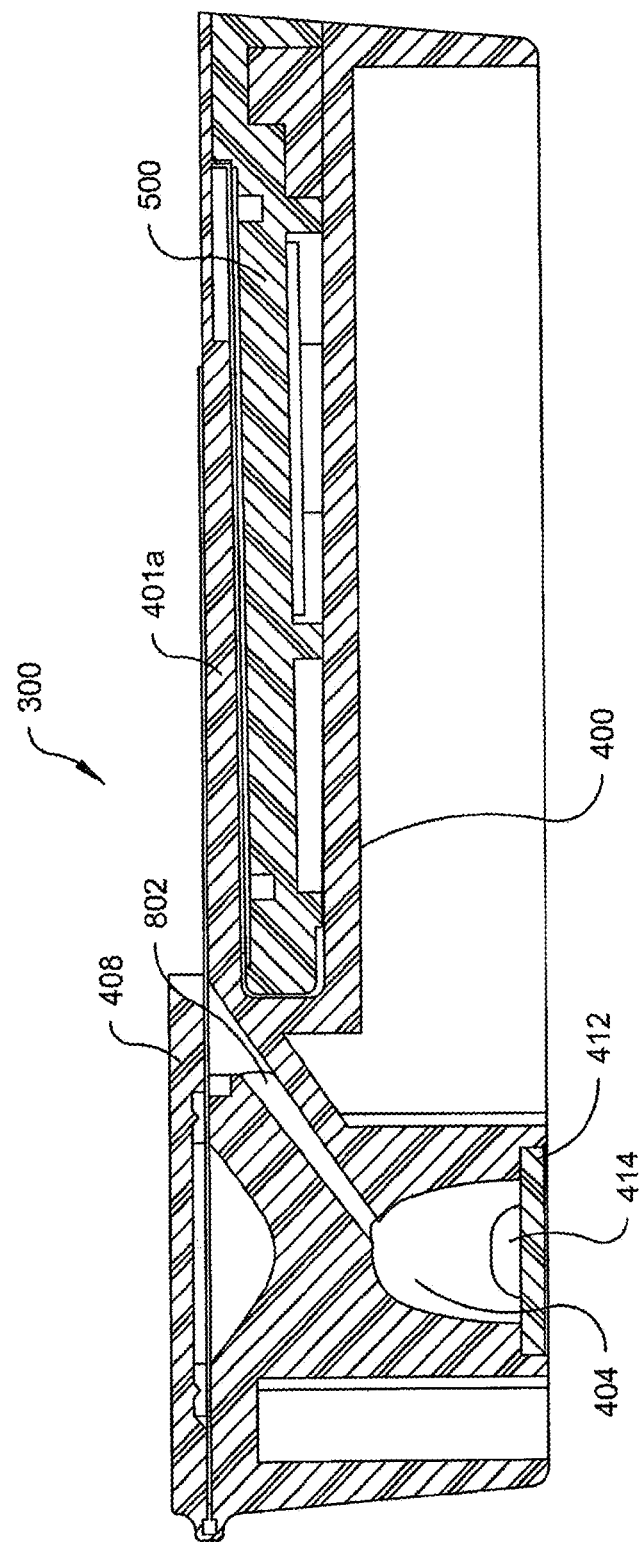
FIG. 8 is a cross-sectional side view of the test cartridge assembly of FIG. 3A.

Referring to FIG. 8, a cross-sectional side elevational view of the test cartridge assembly 300 is shown. It is desirable to mix the reagents 504, 506 and sample 414 in a way to promote mixing beyond molecular diffusion, in order to minimize the duration of the test by ensuring that any infectious agent present in the sample 414 rapidly encounters the reagents 504 and 506. In the preferred embodiment, the minimum diameter of the inlet channel 802 is 0.75 mm. The inlet channel 802 is further preferably offset from the central axis of the reaction chamber 404 in order to promote a clockwise or counterclockwise rotational motion of the reagents 504 and 506 around the central axis of the reaction chamber 404 as the fluids are mixed in order to increase the homogeneity of the mixture.

In the currently preferred embodiment, the inlet channel 802 is approximately tangent to the interior surface of the reaction chamber 404. This is desirable in order to allow the incoming fluid to travel from the inlet channel 802 to the fluid level within the reaction chamber 404 while remaining in contact with the side surface of the reaction chamber 404, which allows for a minimally turbulent flow and minimal introduction of air bubbles into the mixed fluids. Bubbles are undesirable due to the unpredictable refraction of light they cause as light emitted by the reagents 504, 506 interacting with the sample 414 travels through bubbles within the mixed reagents 504, 506 or on the surface of the mixed reagents 504, 506.

In some embodiments of the invention, a stabilizer is included in the reaction chamber 404. The stabilizer may be, for example, Pluronic F68, which is used in cell cultures as a stabilizer of cell membranes by protecting from membrane shearing and additionally as an anti-foaming agent. Certain embodiments of this invention also include at least one additive, such as Pluronic F68, polyethylene glycol, methocel, or the like, located in the reaction chamber 404 for minimizing the formation of bubbles in the reaction chamber 404 during mixing of the sample 414 and the reagents 504, 506. This additive may further include a surfactant, such as Pluronic F68, Polyvinyl pyrolidone, Polyethylene glycol, Polyvinyl alcohol, Methocel (methyl cellulose), or the like. Some embodiments of the present invention also include a device for disrupting individual cells of the sample 414 and particularly the infectious agent within the sample 414 prior to mixing the sample 414 with the reagents 504, 506 for purposes of amplifying the light signal generated by the reagents 504, 506 reacting with an infectious agent within the sample. An example of such a device is a sonicator (not shown).

The axis of the inlet channel 802 is preferably angled above horizontal in order to provide a partially downward direction to the incoming fluid flow to ensure that the reagents 504, 506 are mixed with the fluid residing at the bottom of the reaction chamber 404. In the currently preferred embodiment, the inlet channel 802 is angled above horizontal at an angle of approximately thirty (30) degrees, and additionally the optimum functional range occurs between fifteen (15) degrees and sixty (60) degrees above horizontal. It will be appreciated by those skilled in the art that the arrangement, position and structure of the inlet channel 802 may be varied without departing from the scope of the present invention.

Alternatively, if desired, the reagents 504, 506 may be introduced to the reaction chamber 404 using alternative fluid delivery techniques, such as a vertical channel (not shown) that delivers the reagents 504, 506 to the reaction chamber 404, or delivering the fluid reagents 504, 506 directly on the central axis of the reaction chamber 404 in order to create a column of reagent flowing into the reaction chamber 404 promoting mixing through entrainment. Furthermore, a user may deliver the one or more reagents 504, 506 manually in the same way and, for example, at the same time as the sample 414 is deposited into the reaction chamber 404.

The reaction chamber 404 preferably has a shape that maximizes the amount of photons that are reflected toward the bottom of the reaction chamber 404 to allow the photons to be read by the sensor 206 positioned under the reaction chamber 404 in the analysis portion 200. In the preferred embodiment, the shape of the reaction chamber 404 is a revolved section to facilitate the clockwise or counterclockwise motion of the mixing fluids 414, 504, 506 around the central axis of the reaction chamber 404. Alternatively, if desired, a reaction chamber 404 shape other than a revolved section, such as a rectangular or irregular shape, could be used. In the preferred embodiment, the revolved section used to form the reaction chamber 404 is a portion of an ellipse. This elliptical shape is desirable in order to aid in collecting stray light emitted by the reagents 504, 506 reacting with the sample 414 and reflecting this light toward the surface of the light sensor 206. The reaction chamber 404 shape is preferably generally parabolic. The reaction chamber 404 may be a revolved half of an ellipse with an opening at the top of approximately 2.5 mm, and with the lower diameter located at the major or minor axis of the ellipse and equal to approximately 8 mm.

The surface of the reaction chamber 404 is preferably reflective, in order to further enhance the light collection properties of the elliptical shape. In the preferred embodiment, the maximum diameter of the sensing surface 206a of the sensor 206 is limited in order to achieve the maximum signal to noise ratio of the output of the light sensing circuit 1200 (FIG. 12). The diameter of at least the bottom of the reaction chamber 404 is designed to approximately match the diameter of the sensor 206, which influences the elliptical shape that can be achieved in a reaction chamber 404 designed to hold a specific volume of fluids for a given test type. In the preferred embodiment, the preferable reaction chamber 404 surface color is a partially diffusing white, due to the additional light collection that occurs when light that would not otherwise be reflected directly to the sensor 206 surface 206a is partially diffused by the white surface and a fraction of the light is directed toward the sensor 206 surface 206a. Alternatively, other surface finishes, colors, and materials such as a near-mirror finish aluminum, or a transparent material could be used.

It is desirable for the reaction chamber 404 material to be minimally phosphorescent in order to prevent light emitted from the reaction chamber 404 itself from overwhelming any emitted light from the reagents 504, 506 reacting with the sample 414 and thereby preventing or otherwise affecting detection. Although white polymeric materials such as acrylonitrile butadiene styrene or other such polymeric materials have been found to exhibit a low level of phosphorescence, the additional light collection provided by the combination of light reflection and diffusion has been found to be a benefit to the signal to noise ratio of the output of the light sensing circuit 1200.

Figure 5C:
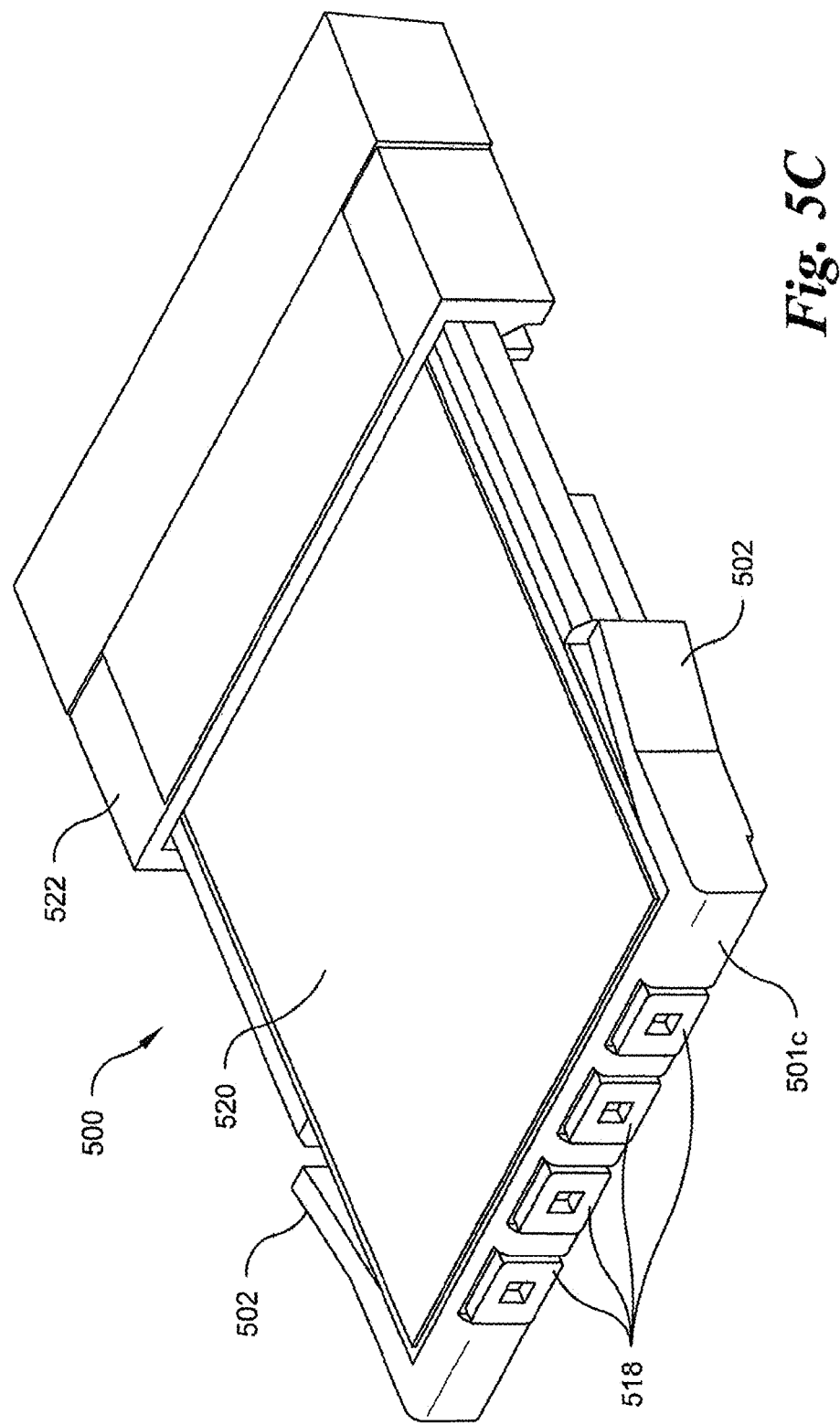
FIG. 5C is a front perspective view of the reservoir card of FIG. 5A in an inserted arrangement to reveal fluid ports.
Figure 5D:
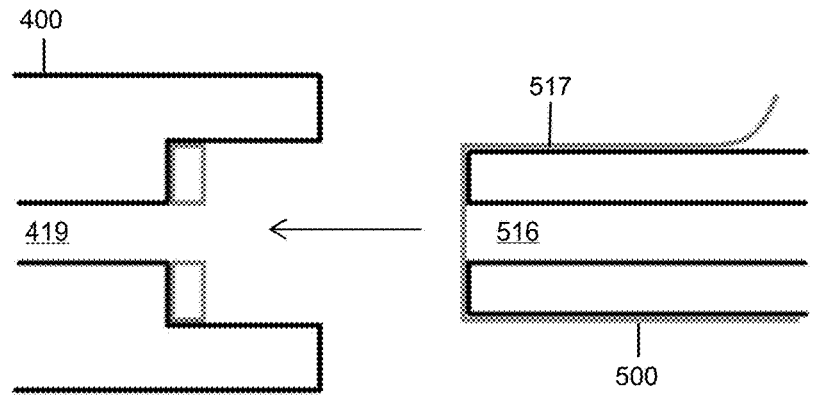
FIGS. 5D, 5E, and 5F illustrate embodiments that include alternate structures for preventing cross-contamination within the reservoir card and the test cartridge base.
Figure 5E:
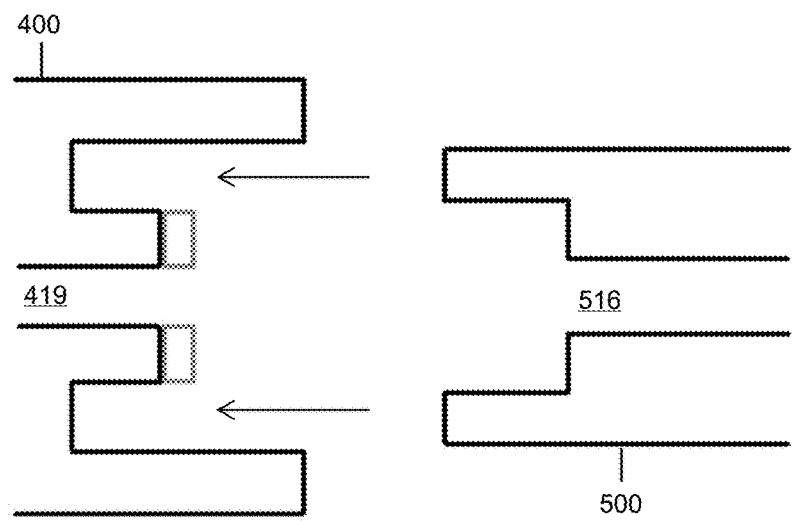
Figure 5F:
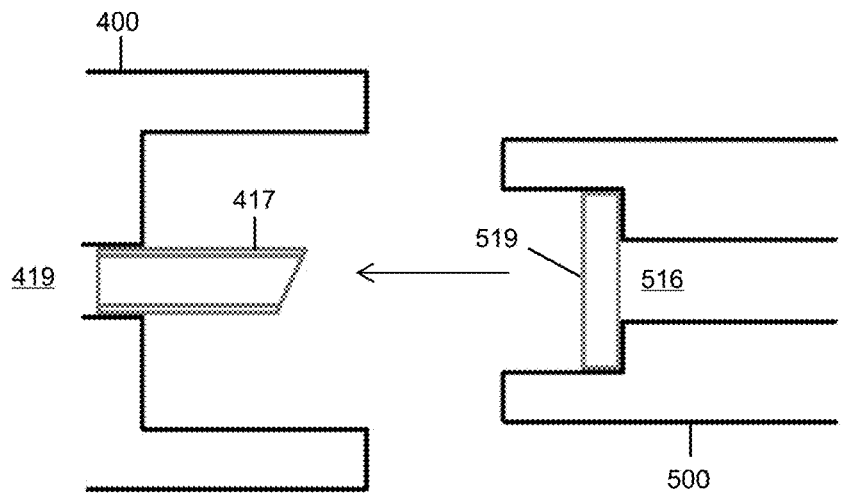

As shown in FIGS. 5A-5C, the reservoir card 500 is comprised of a generally rectangular housing 501. The reservoir card 500 housing 501 is preferably formed of a generally rigid, preferably polymeric material such as polypropylene or some other such polymeric material well-known to those skilled in the art. Referring to FIG. 5B, fluid storage channels 510, 512 are formed into the upper surface 501a of the reservoir card 500 housing 501 in order to provide storage for all of the necessary reagents 504, 506 for performing a specific test type.

In the preferred embodiment, the first reagent 504 is a biosensor reagent capable of emitting light when a specific pathogen or set of pathogens is detected, and the second reagent 506 is a positive control sample, such as anti-Immunoglobulin M (anti-IgM) or digitonin. The second reagent 506 is utilized for the purpose of rapid activation of the first biosensor reagent 504 after the duration of the initial test as a verification of the viability of the biosensor reagent 504. The second reagent 506 functions as a negative result control test, and is therefore optional. That is, the test may be performed without the presence and/or use of the second reagent 506, but in its absence, the accuracy of the test result may be difficult to verify.

The fluid storage channels 510, 512 for storing the reagents 504, 506 are formed to provide a small cross-sectional area, preferably of approximately 1 mm width and 1 mm height. The small cross-sectional area allows the stored reagents 504, 506 to be easily displaced out of the fluid storage channels 510, 512 using one or more additional fluids, such as air. A smaller cross-sectional area is also desirable due to the resulting decrease in thawing time in the occasions where the necessary reagents 504, 506 are required to be stored frozen and are thawed immediately before testing. A thin cover 514, preferably of a polymeric material or the like, is bonded to the reservoir card 500 housing 501 to enclose the fluid storage channels 510, 512 and provide a fluid-tight seal on the top surface 501a of the reservoir card 500 housing 501.

Referring to FIG. 5B, the reservoir card 500 housing 501 also contains a recessed area (not shown) on the bottom surface 501b to contain the RFID tag 508. The recessed area serves to prevent damage from accidental contact with sensitive components of the RFID tag 508. The RFID tag 508 is located within or is secured to the reservoir card 500 in order to minimize user error in associating test cartridge data 300 stored on the RFID tag 508 with the necessary reagents 504, 506 required for specific test types. Use of RFID technology is preferable in order to automate the data transfer between the test cartridge assembly 300 and the testing device 100, thereby minimizing sources of possible user error.

An end face 501c of the reservoir card 500 housing 501 contains a plurality of fluid ports 516a-516d, which make fluid connections with the test cartridge base 400 housing 401, when assembled into the test cartridge assembly 300. Each of the fluid ports 516 are attached to a compressible gasket 518 with an adhesive backing or the like around the perimeter of each fluid port 516. The compressible gaskets 518 create a fluid-tight seal with the test cartridge base 400 housing 401 when the reservoir card 500 is properly installed in the test cartridge base 400 as shown.

In order to prevent contaminants from contacting the fluid ports 516, and to prevent damage to the compressible gaskets 518, the end face 501c of the reservoir card 500 housing 501 is initially covered with a film 520 (see FIG. 5A). In the preferred embodiment, the film 520 is a Polyethylene terephthalate film, or some other flexible polymeric film capable of creating a liquid tight seal with the reservoir card 500 housing 501. The film 520 has selectively applied adhesive backing, and is selectively bonded using the adhesive on a single side of the film 520 to the reservoir card 500 housing 501 in a way such that each fluid port 516 is individually sealed around its perimeter, and one end 520a of the film 520 is permanently bonded to the top face 501a of the reservoir card 500.

Figure 6A:
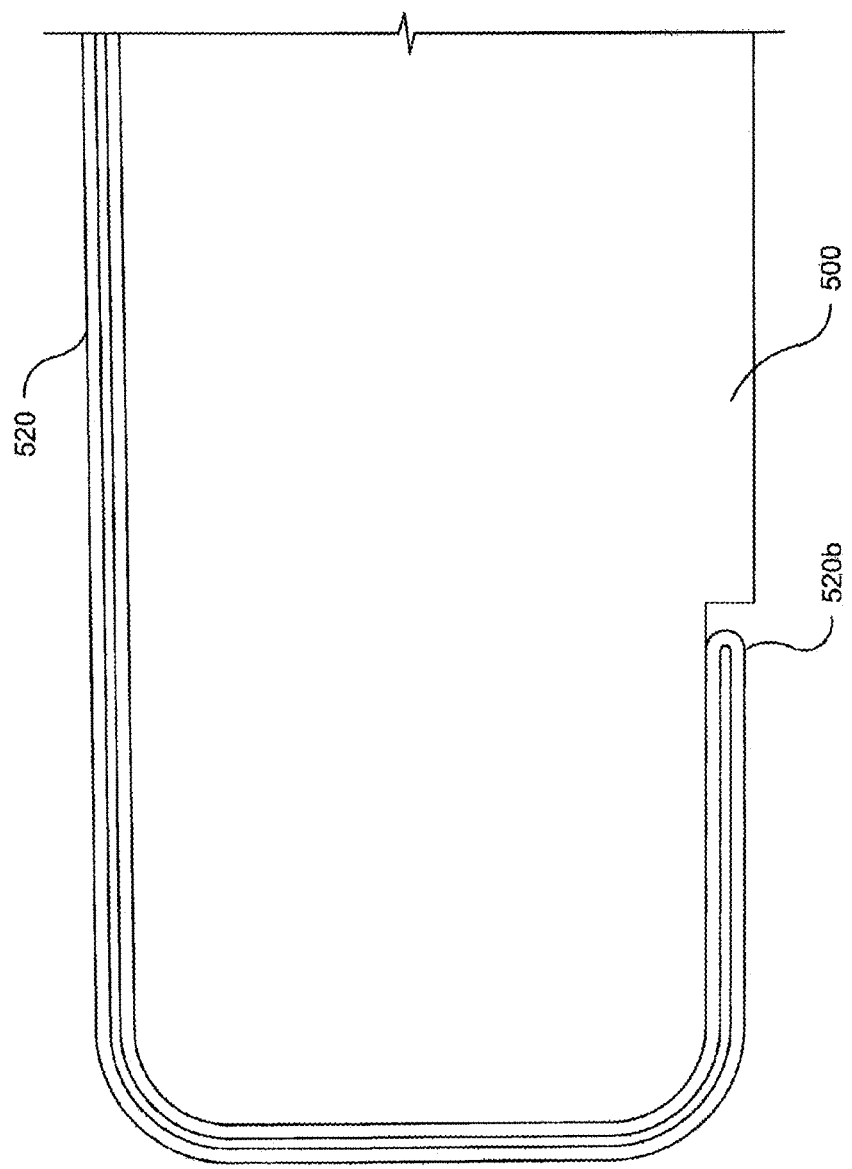
FIG. 6A is a magnified side view of a portion of the reservoir card in the initial arrangement of FIG. 5A with a folded-over film covering the fluid ports.

FIG. 6A is a magnified side elevational view of a portion of the reservoir card 500 in the initial arrangement of FIG. 5A with a folded-over film 520 covering the fluid ports 516. As shown in FIGS. 5B and 6A, the film 520 is laid back upon itself at point 520b so that the remaining end of the film 520 is directed back to the top face 501a of the reservoir card 500. The remaining end 520c of the film 520 is permanently bonded utilizing the selectively applied adhesive to a carrier part 522. The carrier part 522 is preferably made of a generally rigid, polymeric material such as polypropylene, or another such polymeric material known to those skilled in the art.

FIG. 6B is a magnified side elevational view of the portion of the reservoir card 500 in the inserted arrangement of FIG. 5C with the folded-over film 520 retracted to reveal the fluid ports 516. As shown in FIG. 6B, any motion of the carrier part 522 away from the fluid ports 516 results in a peeling motion of the bonded film 520 from the fluid port end 501c of the reservoir card 500 housing 501 which unseals and exposes the fluid ports 516 and their gaskets 518.

There are several actions that occur as the reservoir card 500 is assembled into the test cartridge base 400. As the reservoir card 500 is slid into the receiving slot 402 on the test cartridge base 400 housing 401, the carrier part 522 on the reservoir card 500 mechanically interferes with the top wall of the receiving slot 402 on the test cartridge base 400 housing 401. The reservoir card 500 is shaped so that it cannot be fully inserted into the receiving slot 402 of the test cartridge base 400 in a backwards or top-side-down orientation. When the reservoir card 500 is in the correct orientation, as the user continues to insert the reservoir card 500, the mechanical interference between the carrier part 522 and test cartridge base 400 housing 401 wall causes the carrier part 522 to move relative to the reservoir card 500 away from the fluid ports 516 (See FIG. 5C).

As described above, the motion of the carrier part 522 away from the fluid ports 516 of the reservoir card 500 causes a peeling motion of the film 520 in place over the fluid ports 516 of the reservoir card 500. The peeling of the film 520 exposes the fluid ports 516 and their gaskets 518 on the reservoir card 500 (See FIG. 5C). Preferably, the complete exposing of the fluid ports 516 occurs after the reservoir card 500 has been fully engaged with the receiving slot 402 on the test cartridge base 400 housing 401 so that the fluid ports 516 are protected by the top wall of the receiving slot and are never openly exposed to the external environment. This behavior is desirable to prevent contaminants from contacting the fluid ports 516 and becoming introduced to the reagents 504, 506.

Figure 7:
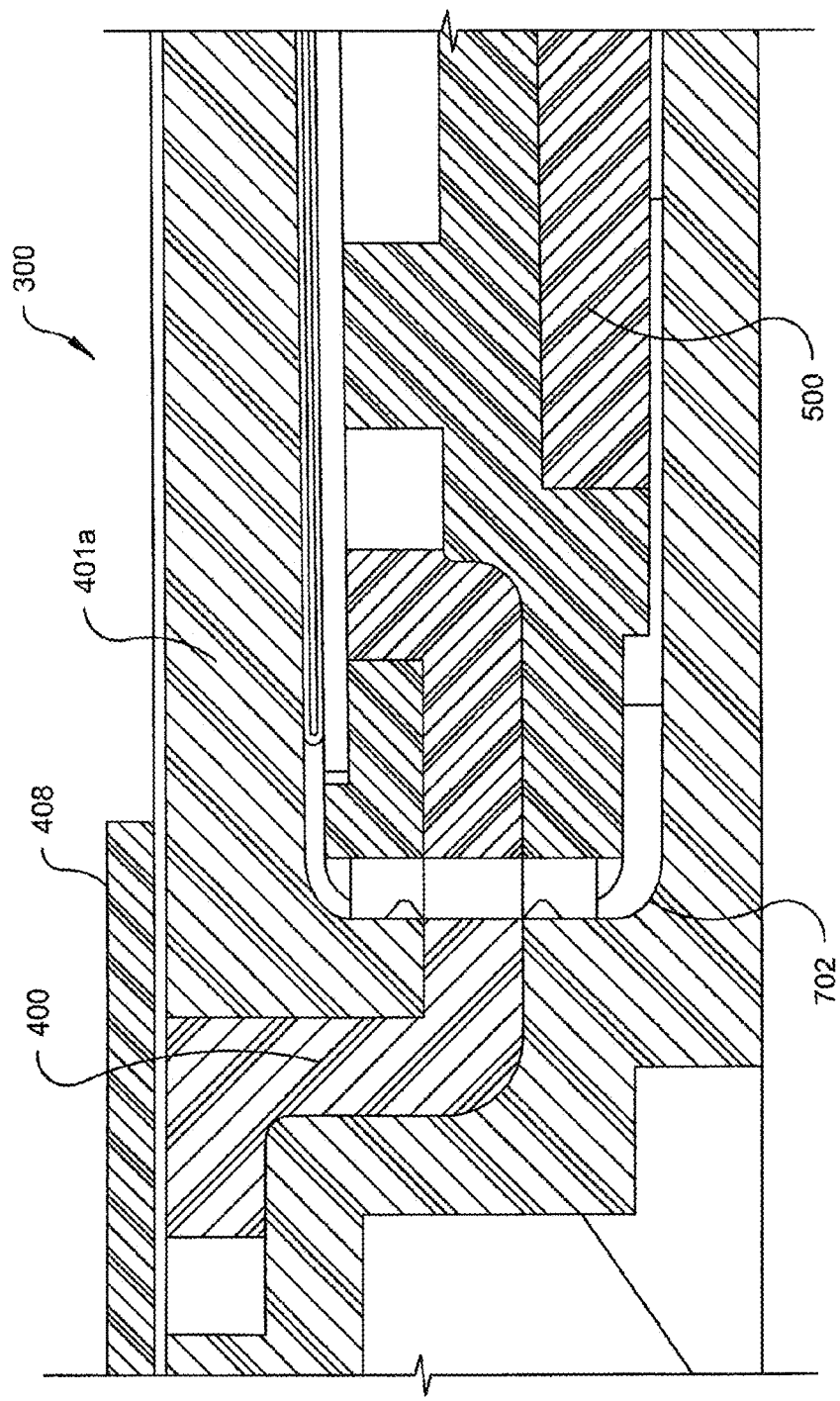
FIG. 7 is a magnified cross-sectional side view of a portion of the test cartridge assembly of FIG. 3A.

As the reservoir card 500 moves fully into the receiving slot 402 on the test cartridge base 400 housing 401, referring to FIG. 7, sealing features 702 present on the test cartridge base 400 housing 401 come into contact with the gaskets 518 of the fluid ports 516 on the reservoir card 500, forming fluid-tight seals. In the presently preferred embodiment, the seal between the gaskets 518 and the sealing features 702 is a face seal. However, other types of seals or sealing features (such as luer seals) could alternatively be employed for providing a fluid-tight seal between the reservoir card 500 and test cartridge base 400 housing 401. Alternative sealing features could include a radially compressible gasket (not shown) forming an annular seal. When the reservoir card 500 has been fully inserted into the receiving slot 402 and the fluid-tight seals have been formed, one way attachment features 502 (FIG. 5B) on the reservoir card 500 housing 501 engage with complimentary retention features (not shown) on the test cartridge base 400 housing 401 in a manner well known in the art to permanently retain the reservoir card 500 in the assembled state with the test cartridge base 400, thereby creating the test cartridge assembly 300.

It will be appreciated by those skilled in the art that while a particular reservoir card 500 component arrangement has been described, the present invention is not limited to this particular arrangement. Possible alternative arrangements include use of only a single reagent, storage of reagents 504, 506 in a larger cylindrical volume, or alternative fluid port protective features, such as pierced films or foils and/or user removed coverings.

Referring to FIGS. 9, 10A, 10B and 10C, a fluid displacement mechanism 900 within the test cartridge base 400 is shown. FIG. 9 is a cross-sectional side elevational view of the test cartridge assembly of FIG. 3A introduced into the analysis portion 200. The plunger 424, which is located in the test cartridge base 400 housing 401, is preferably designed to move air that travels through the air channels 902A-902D in the test cartridge base 400 housing 401, through the sealing features 702 formed between the assembled reservoir card 500 and the test cartridge base 400 housing 401. When actuated by the piston rod 224A, the plunger 424 causes the reagents 504, 506 stored in the reservoir card 500 to be displaced into the test cartridge base 400. As described above, the plunger 424 is preferably actuated by the piston rod 224A in the analysis portion 200.

Figure 10A:
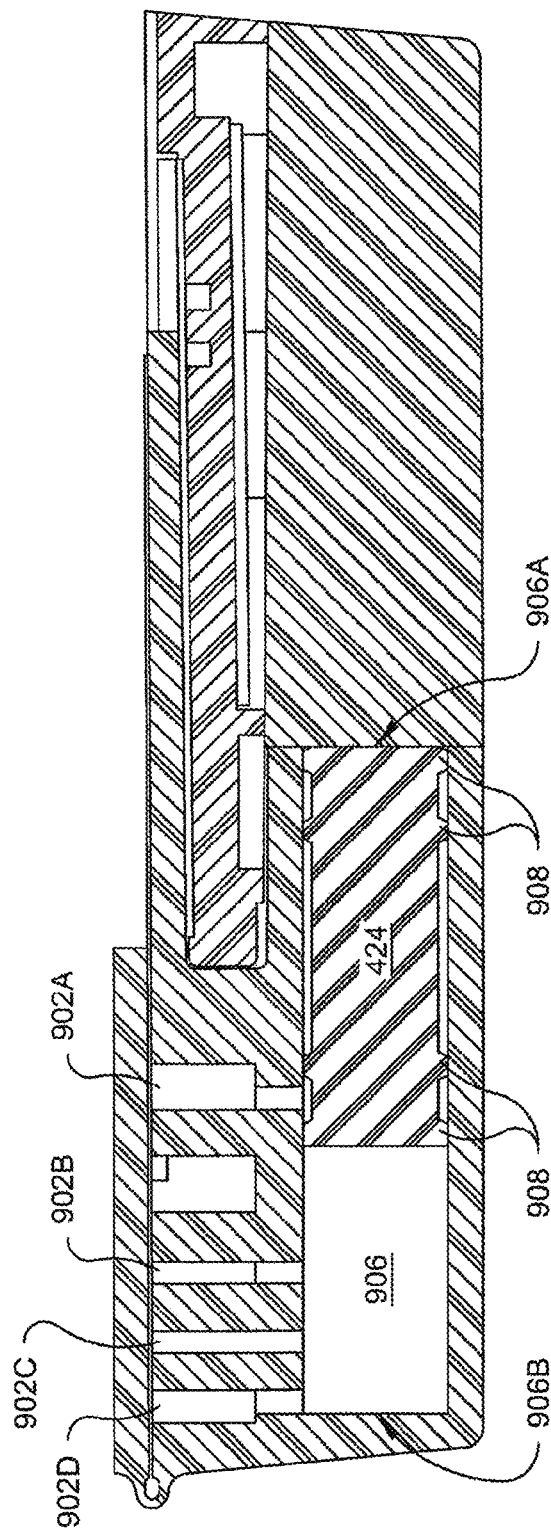
FIG. 10A is a cross-sectional side view of the test cartridge assembly of FIG. 3A with a plunger in an initial position.
Figure 10B:
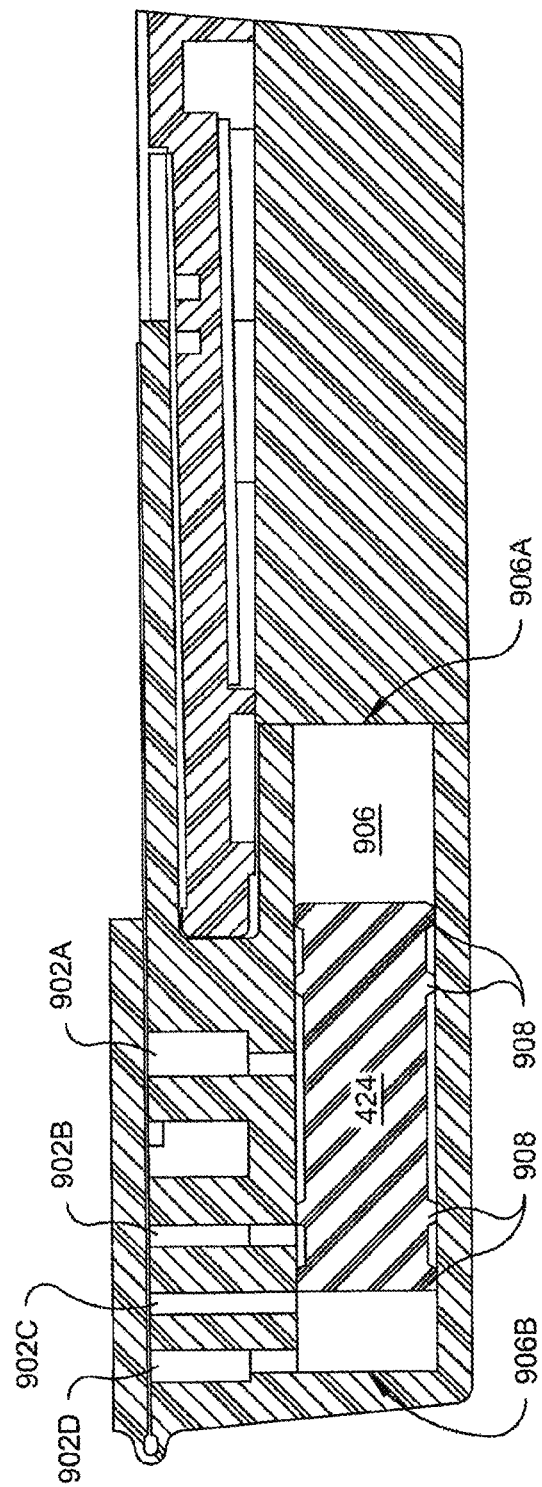
FIG. 10B is a cross-sectional side view of the test cartridge assembly of FIG. 3A with a plunger in a second position.
Figure 10C:
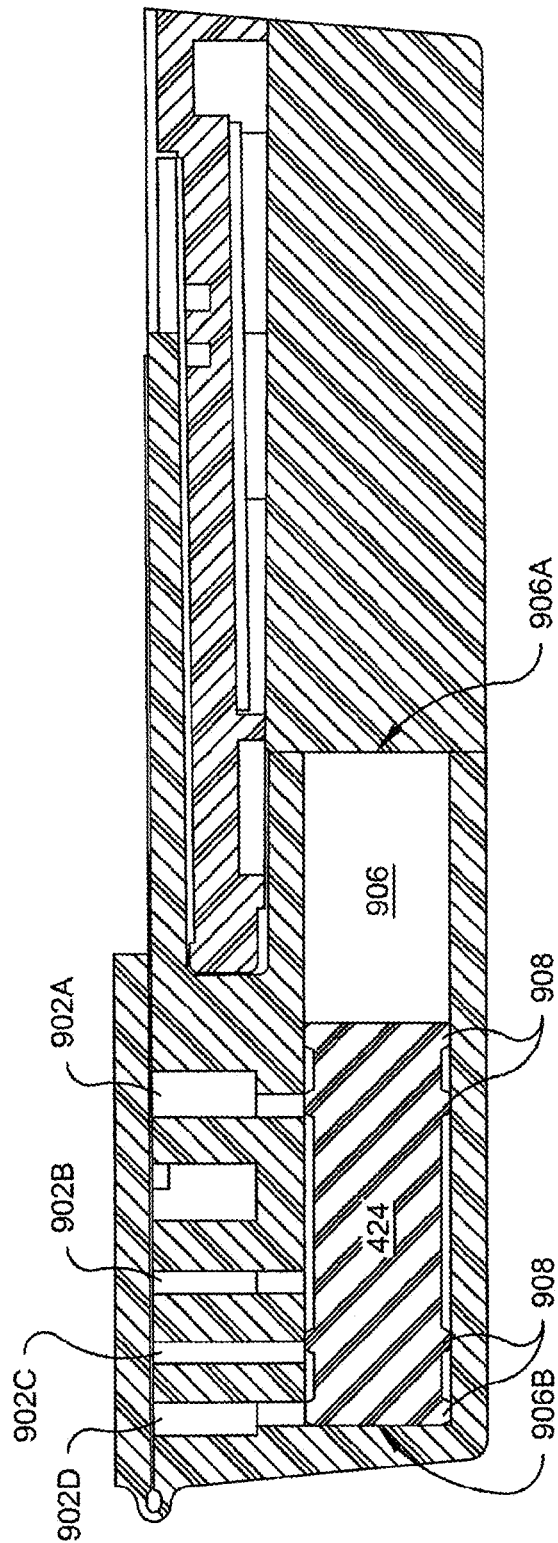
FIG. 10C is a cross-sectional side view of the test cartridge assembly of FIG. 3A with a plunger in a final position.

As they are displaced, the reagents 504, 506 are forced into the test cartridge base 400 housing 401, and eventually into the reaction chamber 404. The design utilizing air to displace the reagents 504, 506 from the reservoir card 500 enables the fluid displacement mechanism 900 components to be located in the test cartridge base 400 housing 401, which allows the reservoir card 500 to achieve a minimal volume to facilitate storage and transport of the reservoir card 500. In the preferred embodiment, the air channels 902A-D leading from the central bore 422 and plunger 424 are designed to produce a staged delivery of the reagents 504, 506 from the reservoir card 500 to the reaction chamber 404. Referring to FIGS. 10A-10C, the delivery of the reagents 504, 506 occurs as air is displaced from the central bore 422 through a series of air channel ports 902 that are alternately sealed, and then opened, as the plunger 424 moves along the central bore 422.

Referring to FIG. 10A, in the beginning or first stage, the plunger 424 is positioned at a beginning end 906A of the central bore 422. Flanges 908 of the plunger 424 initially seal off a first air channel port 902A, which is connected through a fluid port 516C to the storage area 512 for the second reagent 506 in the reservoir card 500 and isolate the first channel port 902A from the other channel ports 902B-D and the first reagent 504.

A second air channel port 902B is open and connected to a fourth air channel port 902D. A third air channel port 902C is open and connected to the first reagent 504 storage area 510. In the preferred embodiment, the first reagent 504 includes the biosensor used for performing the test on the sample 414. As the plunger 424 is actuated by the piston rod 224A, the plunger 424 travels further through the central bore 422, and displaced air from the central bore 422 travels through the third air channel port 902C, displacing the first reagent 504 from the reservoir card 500. The first reagent 504 flows into the test cartridge base 400 housing 401, and eventually into the reaction chamber 404 to mix with the sample 414 in the above-described manner.

As the plunger 424 moves through a second stage toward the second end 906B of the central bore 422, referring to FIG. 10B, the second air channel port 902B becomes sealed off by the flanges 908. However, the sealing of the second air channel port 902B has no effect due to the direct connection of the second air channel port 902B to the fourth air channel port 902D. When the plunger 424 reaches the second stage of FIG. 10B, the entire volume of the first reagent 504 will have been displaced from the reservoir card 500 to the test cartridge base 400 housing 401. At this time, the motion of the plunger 424 is paused with the second air channel port 902B sealed off for the duration necessary to complete the first phase of the test by the testing device 100. In one embodiment, the motion of the plunger 424 is paused for approximately sixty (60) to one hundred twenty (120) or more seconds. The amount of time the plunger 424 is paused preferably depends on the type of test being run by the testing device 100, and is determined based on information provided by a test cartridge 300 RFID tag 508 being read by the testing device 100 after insertion into the cartridge recess 152.

After the first phase of the test is completed, if the second test is to be performed, the plunger 424 is again moved by the piston rod 224A, causing the plunger 424 flanges 908 to seal off the third air channel port 902C and open the second air channel port 902B. As the plunger 424 continues to move through the central bore 422 toward the second end 906B, displaced air from the central bore 422 is forced to travel through the fourth air channel port 902D, to the second air channel port 902B, and through the central bore 422 in the clearance region between the plunger 424 and the central bore 422 surface to the first air channel port 902A. The displaced air that travels through the first air channel port 902A displaces the second reagent 506, which flows into the test cartridge base 400 housing 401, and eventually into the reaction chamber 404 in order to perform the second or negative result verification test phase.

The plunger 424 continues to move through the central bore 422, until contacting the second end 906B of the central bore 422, as shown in FIG. 10C. By this time the majority of the second reagent 506 will have been displaced and flowed into the reaction chamber 404. Upon completion of the plunger's 424 motion from the first end 906A to the second end 906B of the central bore 422, it is preferable that the plunger 424 may not be moved back toward the first end 906A. This one-way motion of the plunger 424 helps to prevent the test cartridge assembly 300 from being reused in a subsequent test.

The use of a single piston rod 224A and a single plunger 424 is desirable to limit the use of additional parts in the test cartridge assembly 300 and testing device 100 for cost reasons, manufacturing complexity reasons, and the reduction of sources of potential interference with the light sensor 206. However, it should be appreciated by those of ordinary skill in the art that the precise structure of the fluid displacement mechanism 900 described above is merely that of a currently preferred embodiment and that variations may be made to the structure of the fluid displacement mechanism 900 without departing from the scope and spirit of this invention. Possible alternative arrangements of the fluid displacement mechanism 900 include utilizing multiple motors to control one specific actuation or more per motor, utilizing multiple plungers to displace one or more reagents 504, 506 per plunger, using plungers to directly displace reagents 504, 506 instead of using air as an intermediary, or using an alternate means of displacing the reagents 504, 506, such as a compressible membrane or blister pack.

Referring to FIG. 11, a functional schematic hardware block diagram 1100 of the electrical/electronic and other related components of the preferred embodiment of the testing device 100 is shown. Operation of the testing device 100 is controlled by a microprocessor 1102. In the preferred embodiment, the microprocessor 1102 is an applications processor, such as the FREESCALE SEMICONDUCTOR model number MCIMX255AJM4A processor, which implements the ARM926EJ-S core with processor speeds up to 400 MHz. Even more preferably, the microprocessor 1102 includes an integrated 10/100 Ethernet controller and a Universal Serial Bus (USB) physical layer (PHY) 1108B. The microprocessor 1102 provides user defined, general purpose input/output (I/O) pins or ports for connection of additional peripheral devices (not shown), as hereinafter described. The microprocessor 1102 core operates between 1.34V-1.45V average power supply voltage from the power supply system 1126. It will be apparent to those skilled in the art that the microprocessor 1102 may be replaced by one or more microprocessors or other control devices such as FPGAs or ASICs, having different and/or additional features and functionalities without departing from the scope of this invention.

The built in USB port 112*b* and USB PHY 1108B integrated into the microprocessor 1102 are used to provide a USB communication port 112*b* that allows the testing device 100 to communicate or receive communications from other USB devices (not shown). The testing device 100 uses a USB client protocol that allows the USB port 112*b* to serve as a client to other USB devices (not shown). The external connection may be used for retrieval and installation of upgraded software, transmission of test records to remote devices (not shown), downloading test information and uploading test results to a host computer, or the like. Other driver circuitry could similarly be used if desired.

The testing device 100 further includes a flash read only memory (ROM) 1104, a dynamic random access memory (RAM) 1106, and an Ethernet PHY interface 1108A, each of which access and are accessed by the microprocessor 1102 by way of individual parallel buses 1110 in a manner well known in the art. In the preferred embodiment, there are at least sixty four megabytes (64 MB) of ROM 1104 and at least sixteen megabytes (16 MB) of SDRAM 1106. The RAM 1106 is a MICRON model MT48LC8M16A2P-7E:G integrated circuit organized by 2 Mb×16 I/Os×4 banks. The RAM 1106 supports software executing within the microprocessor 1102. The ROM 1104 is preferably a SAMSUNG model K9F1208U0C-PIB00 NAND flash memory integrated circuit. The ROM 1104 is a persistent memory that is responsible for retaining all system software and all test records performed by the testing device 100. Accordingly, the ROM 1104 maintains data stored therein even when power to the testing device 100 is removed. ROM 1104 may be rewritten by a procedure well known to those skilled in the art, thereby facilitating the upgrading of system software of the testing device 100 executed by the microprocessor 1102, without having to add or replace any of the memory components 1104, 1106 of the testing device 100. Different models from the same or different manufacturers may alternatively be used for the ROM 1104 and/or the RAM 1106 if desired.

The microprocessor 1102 additionally has an integrated interface for a memory card Secure Digital expansion port and card reader 1112. The SD card expansion port 1112 is located within the testing device 100 to facilitate additional functionality in future iterations of the testing device 100 by introducing an SD memory card (not shown) having additional functionality stored thereon.

The Ethernet PHY interface 1108A is a model DP83640TVV integrated circuit from NATIONAL SEMICONDUCTOR, and provides for a 100 MB per second connection to a local area network (LAN), computer (not shown), or other external device (not shown). The Ethernet PHY interface 1108A negotiates between a connected external device (not shown) and the microprocessor 1102 via its individual parallel bus 1110C.

The testing device 100 requires several regulated voltages to be supplied in order to function properly. The various voltages are provided by a multi-channel power management integrated circuit (PMIC) 1116. The PMIC 1116 addresses power management needs of up to eight (8) independent output voltages with a single input power supply. In the present embodiment, the PMIC 1116 is a FREESCALE MC34704 IC, but other power management circuits may alternatively be used. The PMIC 1116 provides standby outputs that are always actively supplying power to the real-time clock in the microprocessor 1102 and the battery monitor circuit (not shown).

The microprocessor 1102 controls its power supply system 1126, and enters into a sleep mode whenever the testing device 100 is inactive for a predetermined period of time (e.g., 10 minutes). At that time, most internal functions of the microprocessor 1102 are halted, thereby preserving the batteries 116. However, a real time clock (not shown) is kept running to maintain the correct date and time of day for the testing device 100. In addition, one or more sensors, such as the touch screen portion of the LCD 110, are preferably maintained in an active state so that the sleep mode may be exited by, for example, sensing the user depressing any portion of the touch screen, or opening the hinged lid 104 by depressing the actuator 106.

In the event that all electric power to the power supply system 1126 of the testing device 100 is removed, such as when the batteries 116 are replaced, a battery recovery backup (not shown) attached to the microprocessor 1102 maintains the minimal power necessary to power the real time clock so that the testing device 100 can maintain the correct date and time. The ability of the microprocessor 1102 to write to flash ROM 1104 is inhibited whenever power is being removed or restored to the testing device 100 until after the power supply system 1126 and microprocessor 1102 stabilize in order to prevent the accidental altering of the contents of the flash ROM 1102 while power is being cycled.

A first port of the microprocessor 1102 is used for connecting the microprocessor 1102 to the RFID communication circuit 210 via the sensor/RFID board interface 1118 and to the light sensing circuit 1200 (FIG. 12) for receiving data therefrom. A second port of the microprocessor 1102 is used for connecting the microprocessor 1102 to peripherals (not shown) via the Experiment Support Peripheral Interface 1120. The light sensing circuit 1200 will hereinafter be described in greater detail with reference to FIG. 12.

The light sensing circuit 1200 is capable of detecting multiple ranges and types of readings that are necessary for conducting the various types of tests performed by the testing device 100. The light sensing circuit 1200 includes a secondary microprocessor 1202, a fast pulse counter 1204, one or more analog amplifiers and filters 1206, a PMT 206, and a PMT high voltage power supply 218. The PMT 206 detects light signals from the test cartridge assembly 300 on an active surface, and outputs current pulses to the light sensing circuit 1200. In the preferred embodiment, once the reagent 504 has mixed with the sample 414, the PMT 206 begins to analyze the light signature for photons that are not associated with normal radiation, photon emission from the test cartridge base 400 housing 401, and other mechanical noise from the testing device 100. The output current pulses are converted by the light sensing circuit 1200 and relayed by the secondary microprocessor 1202 in a digital format that is sent to the main microprocessor 1102 for analysis.

The spectral response range of the PMT 206 varies from the ultraviolet range to the visible light range (230 nm-700 nm) with a peak response at 350 nm and a photosensitivity response time of 0.57 ns. In the present embodiment, the PMT 206 a model R9880U-110 and high voltage power supply 218 is a model C10940-53, both manufactured by HAMAMATSU PHOTONICS. The secondary microprocessor 1202 is preferably a TEXAS INSTRUMENTS model MSP430F2013IPW processor.

The secondary microprocessor 1202 provides a consistent interface for transmitting data to the main microprocessor 1102. Accordingly, while it is desirable to include the secondary microprocessor 1202 in the testing device 100 within the light sensing circuit 1200 in order to provide future flexibility and ease in implementing additional or alternative sensors 206, or scaling up the light sensing circuit 1200 to include multiple detectors, the secondary microprocessor 1202 is optional. That is, the functionality of the secondary microprocessor 1202 may alternatively be performed by the microprocessor 1102. In this case, the sensor 206 could be connected directly to a serial port on the microprocessor 1102.

PMTs 206 are sensitive to sources of interference, such as temperature changes, electrical fields, magnetic fields, and electromagnetic fields. Thus, the area of the sensing surface of the PMT 206 is susceptible to the output of unwanted signals, or background noise, due to these and other sources of interference. In the preferred embodiment, the diameter of the sensing surface of the PMT 206 is limited to 8 mm in order to limit the generation of background noise signals and increase the signal to noise ratio (SNR) of the output of the light sensing circuit 1200. It will be apparent to those skilled in the art that other PMTs 206 and high voltage power supplies 218 may alternatively be utilized.

Returning to FIG. 11, the LCD 110 is driven by a LCD controller integrated in the microprocessor 1102, which generates the required signaling format to the LCD 110. Accordingly, the LCD 110 is connected to general purpose input/output ports of the microprocessor 1102 via the display/touch panel interface 1122. The LCD 110 preferably includes an on-board drive circuit (not shown) that interfaces with the input/output ports of the microprocessor 1102 via standard data and control signals. The touch screen of the LCD 110 utilizes a four-wire connection for communication with the microprocessor 1102. A speaker 1124 may be connected to the microprocessor 1102 to audibly output sounds, such as warning and error messages, and the like to the user.

Figure 12:
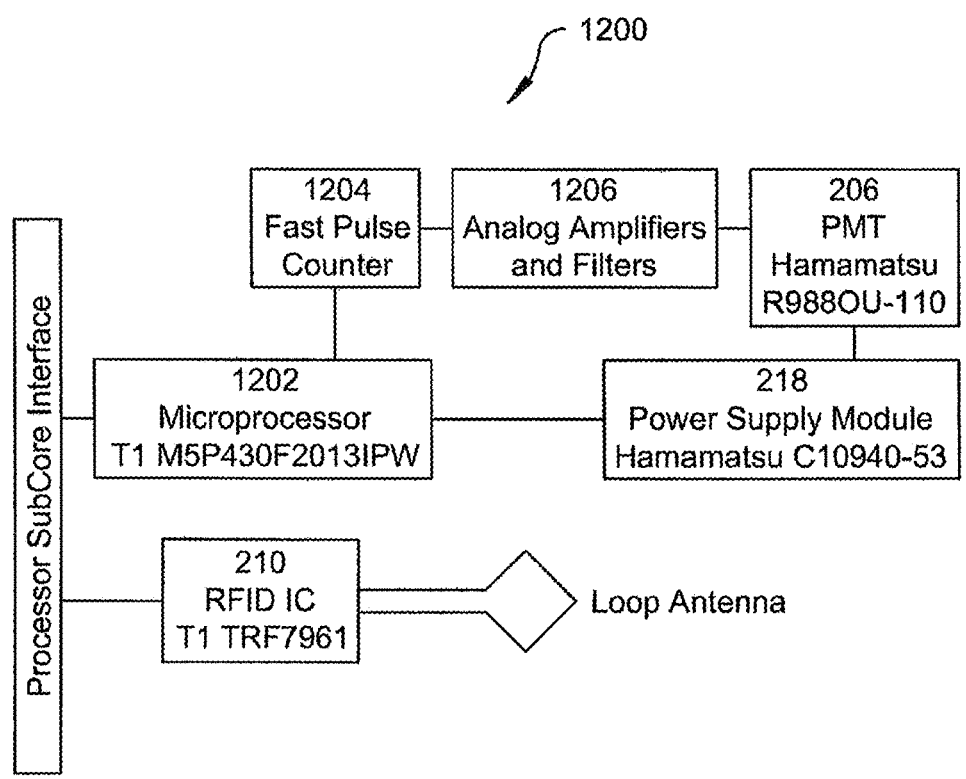
FIG. 12 is a schematic block diagram of a light sensing circuit of the testing device of FIG. 1 according to the preferred embodiment of the present invention.

It should be appreciated by those skilled in the art that the various electrical/electronic components shown in FIGS. 11 and 12 are merely one illustration of the electrical/electronic components of the preferred embodiment of the present invention. Other components may be substituted for or added to any of the components shown without departing from the scope of this invention. In other words, the present invention is not limited to the precise structure and operation of the electrical/electronic and related components shown in FIGS. 11 and 12.

Figure 16:
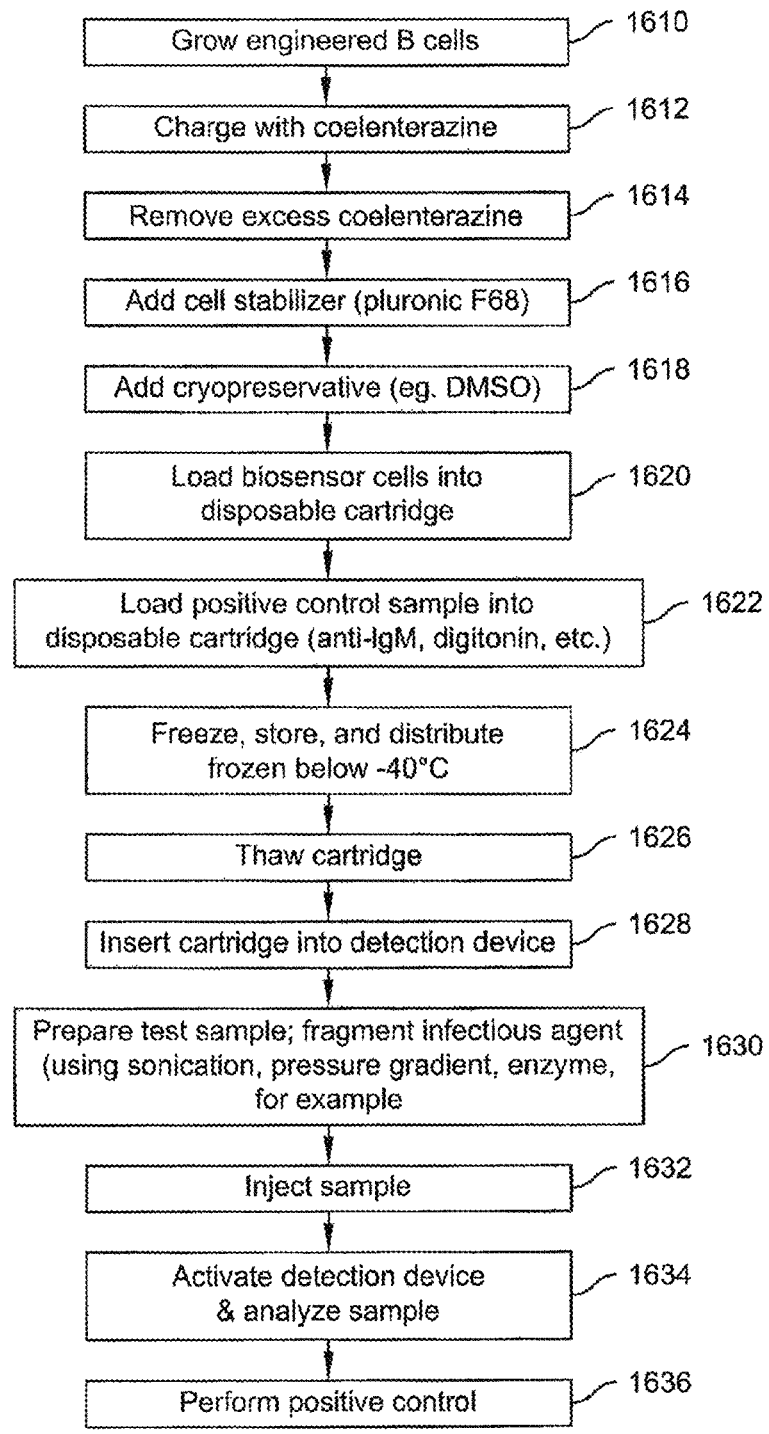
FIG. 16 is a flowchart of steps in which the test cartridge assembly 300 is utilized in conjunction with the testing device 100 for performing a test.

Referring to FIG. 16, a flowchart of steps in which the test cartridge assembly 300 is utilized in conjunction with the testing device 100 for performing a test according to the preferred embodiment of this invention is shown. Before a test begins, a reservoir card 500 is manufactured, preferably outside of the test setting. Engineered B cells are grown at step 1610. The grown cells are charged with coelenterazine at step 1612, and excess coelenterazine is removed at step 1614. A cell stabilizer, such as pluronic F68 is added at step 1616, and a cryopreservative, such as dimethyl sulfoxide (DMSO), is added at step 1618 to complete creation of the biosensor (i.e., reagent 504). The cells are loaded into the reservoir cards 500 at step 1620. At step 1622, the positive control sample (i.e., reagent 506), such as anti-IgM or digitonin, is loaded into the reservoir cards 500. The reservoir cards 500 are then frozen, stored and/or distributed to testing sites at step 1624. Preferably, the cards are frozen and stored at a temperature below approximately negative forty degrees Celsius (−40° C.).

Once the cards have been distributed, before the test begins, at step 1626, the user may be required to prepare a reservoir card 500 of a selected test type by thawing the reservoir card 500 and the reagents 504, 506 contained inside using a specified thawing procedure. Preferably, a thawing procedure is specified when required for a specific reservoir card 500 test type. At step 1628, a user selects the (prepared) reservoir card 500 of the desired test type and assembles the reservoir card 500 into the test cartridge base 400 until the permanent attachment features 502 on the reservoir card 500 housing 501 engage with the retention features in the test cartridge base 400 housing 401. In the currently preferred embodiment, audible (i.e., a click) and/or tactile feedback is evident to the user due to the permanent attachment features 502 on the reservoir card 500 engaging the retention features on the test cartridge base 400 housing 401.

At step 1630, the user optionally prepares a sample 414 by, for example, fragmenting any infectious agent present in the sample 414 using sonication, pressure gradient, and/or enzyme treatment, or the like. Several techniques may be used, including: (i) an enzyme such as lipase to release O-antigens from the cell surface (part of LPS); (ii) sonication to fragment the cells; (iii) a French Press or equivalent to fragment the cells; or (iv) a chemical treatment to release LPS from the cells. At step 1632, the user employs a sample deposition tool to pierce the perforated film 410 on the test cartridge base 400 above the reaction chamber 404 and deposit a very small quantity (e.g., thirty micro Liters) of a sample 414 of a suspected infectious agent directly into the reaction chamber 404 within the test cartridge base 400. The user then removes the sample deposition tool and closes the test cartridge base 400 integral hinged lid 408, ensuring that the retention features 408a and 408b engage with the slots 420a and 420b on the test cartridge base 400 housing 401. The test cartridge base 400 hinged lid 408 is retained in the closed position, and the compressible gasket 418 on the top surface of the test cartridge base 400 is engaged by the lid 408 to form a fluid-tight seal. At this time, the reagents 504, 506 stored inside the reservoir card 500 must be fully thawed in order to proceed with the rest of the test. Alternatively, the user could assemble the reservoir card 500 into the test cartridge base 400 after depositing the sample 414 in the reaction chamber 404 or before the reagents 504, 506 are thawed. Further, the sample 414 may be deposited into the reaction chamber 404 after the test cartridge assembly 300 has been inserted into the testing device 100.

Referring to FIGS. 1C and 3C, the bottom of the test cartridge assembly 300 is designed to be placed into the cartridge recess 152 in order for the lens 412 of the reaction chamber 404 to align with the sensor 206. The test cartridge assembly 300 and cartridge recess 152 are preferably shaped in a way that the test cartridge assembly 300 cannot be fully inserted in an improper orientation and/or the testing device 100 hinged lid 104 will not be able to close if the test cartridge assembly 300 is introduced into the analysis portion 200 in an improper orientation.

When the user inserts the test cartridge assembly 300 into the cartridge recess 152 in the proper manner, a physical process begins a chain reaction of physical and electronic processes within the testing device 100 to perform the desired test on the sample 414 at step 1634 and, if necessary, a positive control test at step 1636. The user closes the hinged lid 104 of the testing device 100, which mechanically latches in the closed position. The testing device 100 is capable of detecting when the hinged lid 104 is closed, and sends a signal to the microprocessor 1102, which activates the RFID communication circuit 210 for data transmission to and/from the RFID tag 508 via the RFID communications circuit 210.

Figure 13A:
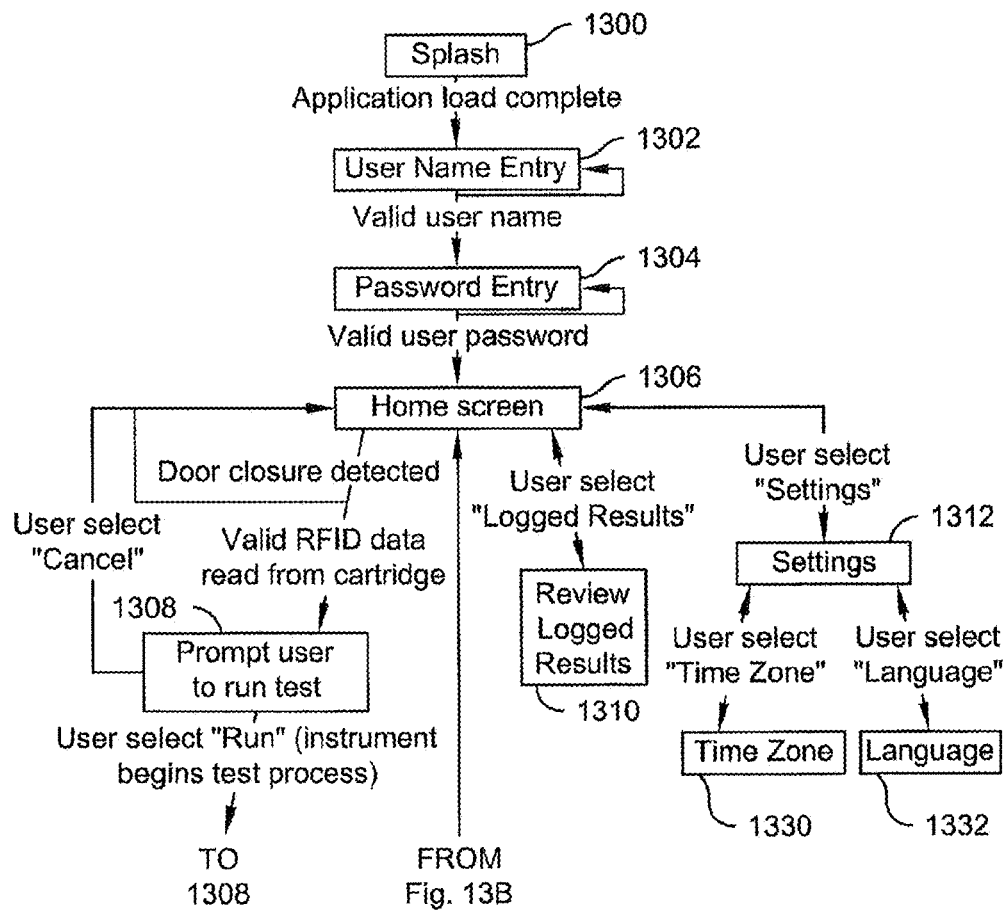
FIGS. 13A and 13B are a flowchart of steps of a control application of the testing device of FIG. 1 according to the preferred embodiment of the present invention.
Figure 13B:
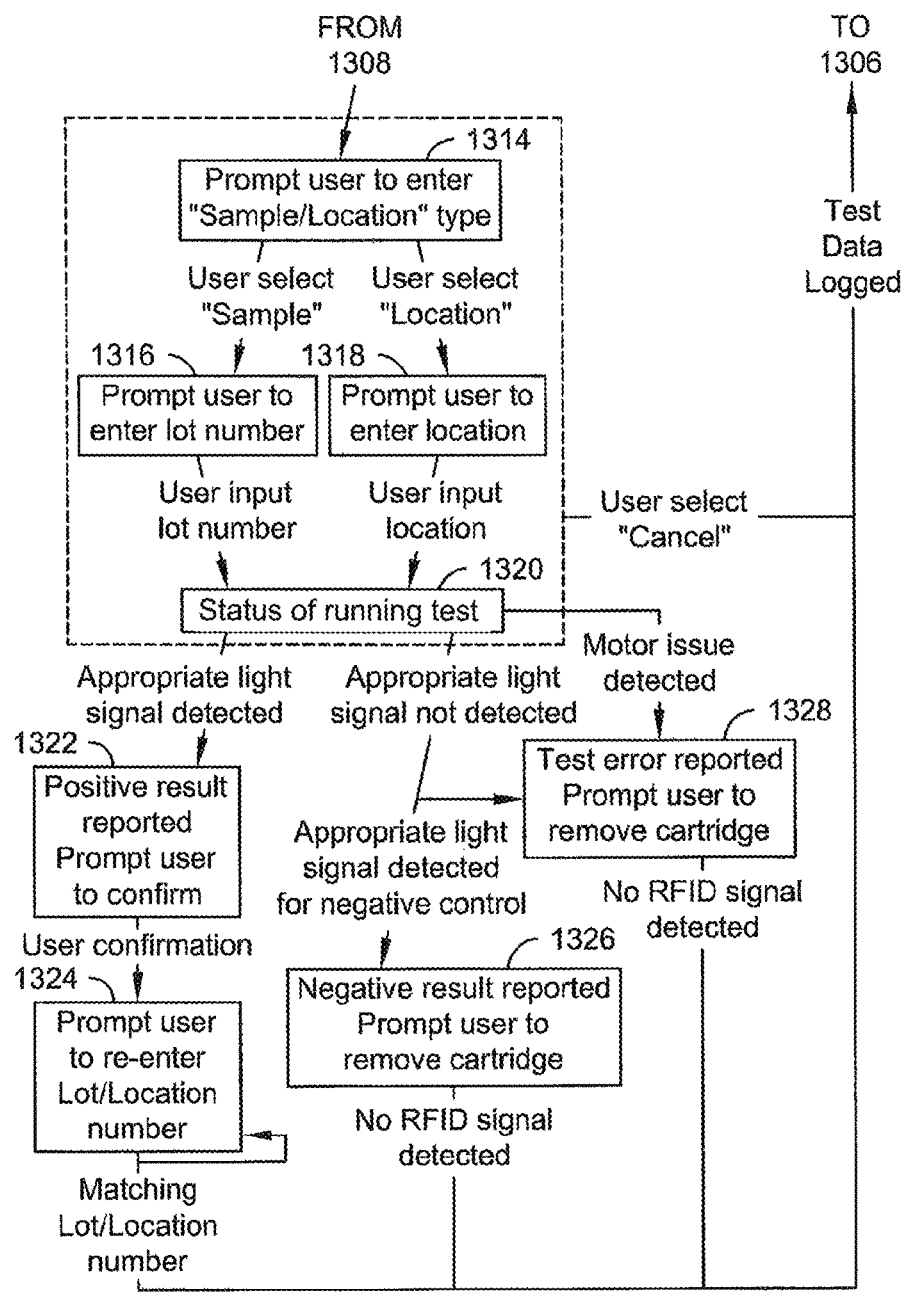

At this time, the RFID tag 508 located within the test reservoir card 500 is placed in the path of the RFID communications circuit 210 within the analysis portion 200. In the present embodiment, the RFID tag 508 is a RI-116-114A-S1 from Texas Instruments, which operates at 13.56 MHz and contains 256 bits of user memory for read/write functionality. The testing device 100 reads detailed information for the test to be performed from the test cartridge assembly 300 RFID tag 508 via RFID. Information which may be communicated to and from the RFID tags 508 includes test lot or sample origin, the specific test to be performed, information concerning the identity of a particular test cartridge, as well as other information. The testing device 100 also writes a value to the test cartridge RFID tag 508, which signifies that the test cartridge assembly 300 has been used to perform a test. The writing of the RFID tag 508 prevents the test cartridge assembly 300 from being reused in the same or any other compatible testing device 100 in the future. Referring to FIGS. 13A and 13B, the testing device 100 prompts the user to confirm the test type and to start the test via a user interface 1400 (FIG. 14) displayed on the LCD 110, which will hereinafter be described in greater detail.

Referring to FIGS. 2 and 9, when the user chooses to start the test, the microprocessor 1102 sends a signal to actuate the motor 226, which drives the piston 224 and piston rod 224A forward to engage the fluid displacement mechanism 900, and to complete the introduction of the first reagent 504 to the reaction chamber 404 in the manner described above. The piston rod 224A also preferably functions as a hinged lid 104 interlock. Thus, once the piston 224 begins to move under the force of the motor 226 at the start of the test, the piston rod 224A moves beneath the actuator 106. When the piston rod 224A is beneath the actuator 106, mechanical interference between the two prevents the user from pushing down the actuator 106 and opening the lid 104 as a precaution against user error while a test is in process. The piston rod 224A remains beneath the actuator until the test is complete and the piston 224 is fully retracted. Simultaneously to completing the first stage of the fluid displacement mechanism 900, the piston rod 224A moves the sliding shutter 236 to its second position which exposes the surface of the sensor 206 to light emitted from the reaction chamber 404 of the test cartridge assembly 300 via the sliding shutter aperture 238.

Since the reaction process preferably begins as soon as the fluid displacement mechanism 900 within the test cartridge assembly 300 completes the first reagent 504 introduction to the reaction chamber 404, the light sensing circuit 1200 is also activated at this time to detect any light emissions that may occur even before the user makes the appropriate data entry, as will hereinafter be described in greater detail. If the light sensing circuit 1200 detects an appropriate light signal, the microprocessor 1102 stores and reports a positive result, the light sensing circuit 1200 is turned off and the motor 226 moves to retract the piston 224 to its initial position.

The plunger 424 of the tested test cartridge assembly 300 remains at its final position even after the piston 224 has been retracted. The user may then open the hinged lid 104 by pressing the actuator 106 and remove the used test cartridge assembly 300 for proper disposal. The test sample 414 and the reagents 504, 506 are all sealingly contained within the test cartridge assembly 300. The user may also confirm a result of the test within the user interface (FIG. 15) displayed on the testing device 100 LCD. Alternatively, if a predetermined length of time (e.g., 60-120 seconds) elapses during the initial test and the light sensing circuit 1200 has not detected an appropriate light signal, the motor 226 preferably moves to drive the piston 224 further into the fluid displacement mechanism 900 until completion of the introduction second reagent 506 into the reaction chamber 404 for the performance of the second test, as described above.

If the light sensing circuit 1200 does not detect an appropriate light signal as a result of the second test, the microprocessor 1102 stores and reports an error message. However, if as a result of the second test the appropriate light signal is detected by the light sensing circuit 1200, the microprocessor 1102 stores and reports a negative result. At this time, the light sensing circuit 1200 is turned off and the motor 226 moves to retract the piston 224 to its initial position. The user may then remove the used test cartridge assembly 300 for proper disposal. At this time, the testing device 100 is reset and is ready for receiving another test cartridge assembly 300. Subsequent testing may be conducted in the same manner (using a new test cartridge assembly 300) as described above.

As previously discussed, the testing device 100 has the capability of performing a variety of different real-time (or near real-time) tests using a single disposable test cartridge assembly 300 containing a reservoir card 500 which has been specifically designated to perform a particular test. Each reservoir card 500 contains a predetermined reagent mixture 504, 506 for performing a particular test. The RFID tag 508 within the reservoir card 500, as well as the reservoir card labeling (not shown) identifies the particular test that reservoir card 500 is to perform, as well as the relevant control parameters for the particular test. In this manner, the testing device 100 is adapted for automatic customization, through software, for the performance of various tests.

An exemplary first reagent 504 is a biosensor reagent which includes a human B lymphocyte engineered to express a bioluminescent protein and at least one membrane-bound antibody specific for a predetermined infectious agent. With regard to biosensors, cell-based biosensor (CBB) systems that incorporate whole cells or cellular components respond in a manner that can offer insight into the physiological effect of an analyte. As will be appreciated by those skilled in the art, cell-based assays (CBA) are emerging as dependable and promising approaches for detecting the presence of pathogens in clinical, environmental, or food samples because living cells are known to be extremely sensitive to modulations or disturbances in "normal" physiological microenvironments. Therefore, CBB systems have been employed to screen and monitor "external" or environmental agents capable of causing perturbations of living cells (see, for example, Banerjee et al., Mammalian cell-based sensor system, Adv. Biochem. Eng. Biotechnology, 117:21-55 (2010), which is incorporated by reference herein.)

Compared with traditional detection methods (e.g., immunoassays and molecular assays such as PCR), a biosensor provides several advantages including, (i) speed, i.e. detection and analysis occurs in several seconds to less than 10 minutes; (ii) increased functionality, which is extremely important for reporting active components such as live pathogens or active toxins, and (iii) ease of scale-up for performing high-throughput screening.

An aequorin-based biosensor system is utilized with certain embodiments of the present invention. Aequorin is a 21-kDa calcium-binding photoprotein isolated from the luminous jellyfish *Aequorea victoria*. Aequorin is linked covalently to a hydrophobic prosthetic group (coelenterazine). Upon binding of calcium (Ca2+) and coelenterazine, aequorin undergoes an irreversible reaction, and emits blue light (preferably 469 nm). The fractional rate of aequorin consumption is proportional, in the physiological pCa range, to [Ca2+]. Application of the aequorin-Ca2+ indicator to detect *E. coli* contamination in food products was reported in 2003 (see, Rider et al. A B cell-based sensor for rapid identification of pathogens, Science, 301(5630):213-5 (2003), which is incorporated by reference herein). In Rider, engineered B lymphocytes were used to express antibodies that recognize specific bacteria and viruses. The B lymphocytes were also used to express aequorin, which emits light in response to the calcium flux triggered by the binding of a cognate target to the surface-antibody receptor. The resulting biosensor cell emitted light within minutes in the presence of the targeted microbes. To create such biosensor cells, antibody heavy and light chains with variable regions were cloned and expressed in a B-lymphocyte cell line. The resulting immunoglobulins become part of a surface B-cell-receptor complex, which includes the accessory molecules immunoglobulin.alpha. (Ig.alpha., or CD79a) and immunoglobulin.beta. (Tg.beta., or CD79b). When the complex is cross-linked and clustered by polyvalent antigens, such as microbes, a set of signaling events quickly leads to changes in the intracellular calcium-ion concentration, which then causes aequorin to emit light. This mechanism essentially hijacks the B-cell's intrinsic capacity to specifically recognize the antigen presented in the *E. coli* by the B-cell membrane IgG antibody, and this binding triggers a transient Ca2+ influx to cytosol, which binds the aequorin proteins engineered in this B-cell, and subsequently emit blue light. See, Reiman, Shedding light on microbial detection, N England J Med, 349(22):2162-3 (2003), which is incorporated by reference herein, in its entirety.

Selection of an appropriate B cell is important to the described testing. Therefore, any proposed cell line should be tested to confirm that the B cell receptor signaling pathway is fully functional. Individual B cell clones having the aequorin gene should be tested to identify a particular clone with high aequorin activity, as significant variation from one clone to the next is possible (see, generally, Calpe et al., ZAP-70 enhances migration of malignant B lymphocytes toward CCL21 by inducing CCR7 expression via IgM-ERK1/2 activation, Blood, 118(16):4401-10 (2011) and Cragg et al., Analysis of the interaction of monoclonal antibodies with surface IgM on neoplastic B-cells, Br J Cancer, 79(5/6): 850-857 (1999), both of which are incorporated by reference herein in their entirety).

A high-aequorin expressing B cell is important for achieving high levels of sensitivity when using this detection system. In an exemplary embodiment, the receptor response for the biosensor was verified by using the Ramos human B cell line. Ramos cells are first transfected with the aequorin gene and the transfected cells were then selected for the aequorin expression for two weeks. Thereafter, mixed Ramos cells are charged with coelenterazine (CTZ), and stimulated with anti-IgM Ab. The elicited flash signal is captured by a luminometer.

Figure 17:
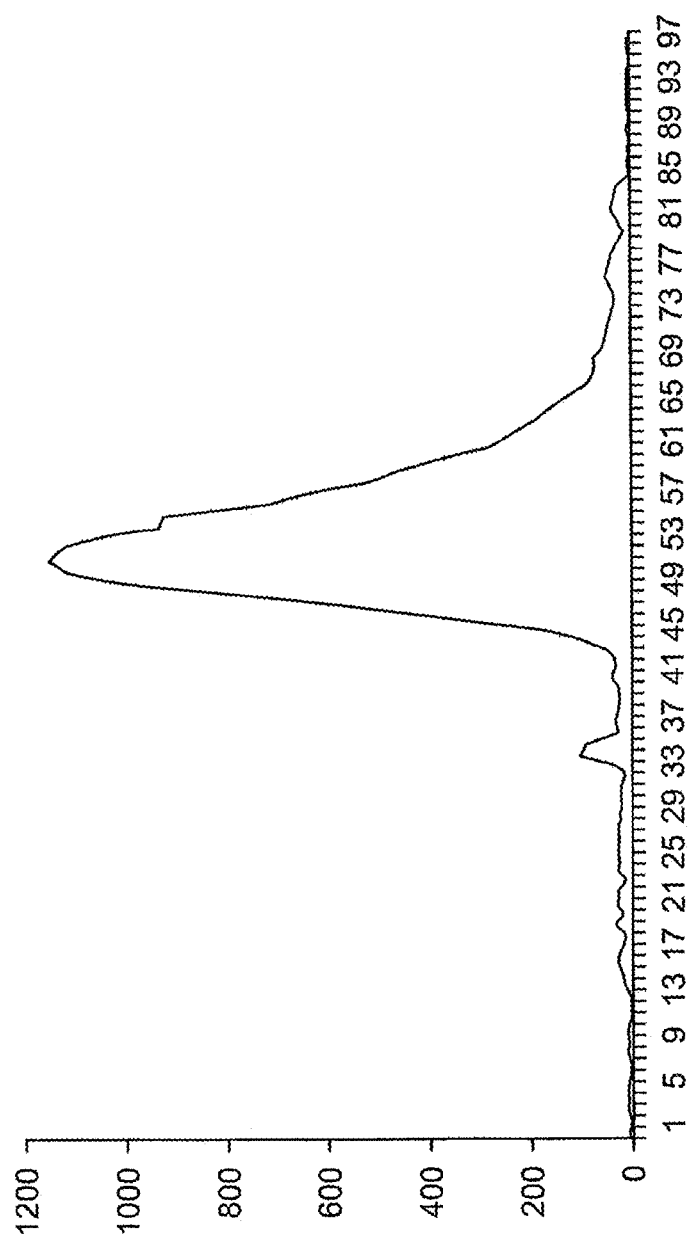
FIG. 17 is a chart illustrating the effectiveness of the system of the present invention with regard to detecting the presence of one or more infectious agents in a biological sample.

As shown in FIG. 17, anti-IgM stimulation causes an expected sizeable and prolonged flash (from 45 to 65 seconds). In FIG. 17, the Y-axis represents the amount of light flashing, and the X-axis represents the reaction time in seconds. At thirty (30) seconds, the anti-IgM solution is injected into the Ramos-aequorin cell solution. The first spike (from 30-37 seconds) is a noise signal, and the second larger and longer peak is the biological response to anti-IgM stimulation. To improve the overall signal/noise ratio, the CTZ is removed from the CTZ-charged Ramos-aequorin cells solution. Removal of CTZ from the cell solution decreases the noise signal from around one hundred fifty (150) to about fifty (50), without significant compromise of the amount of the true peak signal.

In accordance with the present invention, an exemplary protocol for cell handling and flash-testing includes: (i) culturing Ramos-aequorin cells with a regular culture medium and keeping these cells healthy (i.e., viability>98%); (ii) charging the Ramos-aequorin cells with CTZ at a final concentration of 2 μM, the cell density being 1-2 million per milliliter; (iii) charging the cells at 370° C. with 5% $CO_2$ in an incubator for at least 3 hours; (iv) removing the charging medium containing CTZ; (v) flash testing by taking 200 μL cell solution plus 30 μL stimulants (anti-IgM) and reading with a luminometer; and (vi) confirming the CTZ and aequorin functionality by adding 30-40 μL digitonin (770 μM).

The testing device 100 is preferably controlled by an operating system executed by the microprocessor 1102. In the present embodiment, the operating system is preferably a custom designed and programmed application running in the Linux environment. The operating system provides input/output functionality, and power management functions, as described. The custom application includes a simple, menu-based user interface, as shown in FIGS. 14 and 15; parameter-driven functions to control and analyze the tests performed by the testing device 100; and a file system to store test protocols and results. Stored test results can be recalled, displayed or printed out. The software allows for the addition of protocols for new tests through file downloading, or the like.

The user interface 1400 of FIG. 14 is preferably menu driven, with a series of items selectable by a user using menus provided on the touch screen LCD 110. Preferably, the user interface 1400 presents a series of choices that allows navigation to and through each specific test until completion thereof. In the present embodiment, the user interface 1400 allows the user to return to the previous screen by using a back key provided on the LCD and touch screen. However, use of the back key while testing is not allowed unless the test is cancelled or aborted. A selected action may proceed through a series of steps with each step being indicated by a new prompt to the user.

FIGS. 13A and 13B are a flowchart showing the basic flow of a preferred embodiment of the computer software employed by the testing device 100. It will be appreciated by those skilled in the art that the software may function in a slightly or completely different manner than the manner shown in FIGS. 13A and 13B, which is included merely to illustrate a currently preferred way for the software to function.

The process begins at step 1300, where a splash screen is presented to the user on the display 110 while the application completes loading on the testing device 100. At step 1302 and 1304, a user is prompted with a user name and password entry process. The testing device 100 verifies that the entered user name and password are valid, and proceeds to a home screen 1400 (FIG. 14) at step 1306. A user identifier (e.g., a five-digit code) uniquely identifying the user performing the test is preferably stored by the testing device 100 as part of a test record.

The user selects one or more actions and/or functions of the testing device 100 to be performed from the home screen 1400, including running a test (step 1308) by inserting a test cartridge assembly 300, reviewing logged results (step 1310) by pressing Test Log button 1402 or configuring settings (step 1312) such as Time Zone (Step 1330) or Language (Step 1332) by pressing button 1404. Preferably, the user selects the desired action using the touch screen LCD 110 of the testing device 100.

If the user inserts a test cartridge assembly 300 into the testing device 100 and closes the hinged lid 104, the RFID communications circuit 210 is activated after the hinged lid 104 is closed, and the RFID tag 508 or other identification on the installed test cartridge assembly 300 identifies the type of test that the testing device 100 is to perform.

Preferably, each RFID tag 508 stores a character string, which encodes the particular type of test for the test cartridge assembly 300, an expiration date for each test cartridge assembly 300, a test cartridge assembly 300 serial number, which may include a testing solution lot number, whether the test cartridge assembly 300 has previously been tested within a testing device 100, as well as other information pertaining to a particular test cartridge assembly 300. Taken together, the information presented in the RFID character string uniquely identifies each test cartridge assembly 300. The test cartridge assembly 300 information is entered into the testing device 100 when the test cartridge assembly 300 is inserted into the cartridge recess 152 in the analysis portion 200 and the hinged lid 104 is closed. The process checks the scanned test cartridge RFID tag 508 data to confirm that the test cartridge has not been used before. RFID tag 508 data scanned from the test cartridge are accepted as valid if the RFID communications circuit 210 detects no RFID transmission error during the scanning process and the data format of the RFID tag 508 is valid. Upon determining that the hinged door 104 is closed and that the data read from RFID tag 508 is valid, the Run test option of step 1308 is automatically selected, and the user is prompted to confirm that the testing device 100 is to run the test.

While the test begins, the user begins the required data entry. The user is prompted to enter the specific numeric code of the sample 414 into the touch screen LCD 110 at step 1314, where the user is prompted to enter a "Sample/Location" type. In the preferred embodiment, the numeric code of the sample 414 comprises a five digit number that relates to a lot or environment of the sample 414. If the user selects "Sample," at step 1316, the user is prompted to enter a lot number using the touch screen LCD 110. If the user selects "Location," at step 1318, the user is prompted to enter a location using the touch screen LCD 110.

Upon receiving the sample specific code, the information received from the RFID tag 508 of the test cartridge assembly 300 and the received user data entry are compared to all stored test records, as well as the data received from the RFID tag 508 signifying whether the test cartridge assembly 300 has previously been tested, and rejects the test cartridge assembly 300 if that test cartridge assembly 300 has been tested before.

The information read from the RFID tag 508 is also used to identify the particular test to be performed by the testing device 100, and to select the appropriate test protocols. Protocols to be selected include test timing, light reading requirements from the light sensing circuit 1200, and the like for the particular test to be performed. The parameters from a test control table stored in the ROM 1104 specify how each step of the test data acquisition and analysis is to be performed, including alternate software routines where necessary. In this manner, new or modified test parameters can be installed by downloading new test control tables and, if necessary, supporting software modules, without modification of the basic operating or application software. Information from test control tables is stored in the ROM 1104 for each diagnostic test which could potentially be performed utilizing the testing device 100. In alternate embodiments, additional information relating to the test samples 414 may also be included in the test initiation process of the testing device 100. Such additional information may include handling requirements, quarantine requirements and other anomalous characteristics of test samples 414.

The testing device 100 performs the test on the sample 414 while the user enters the sample 414 specific numeric code, and continues to perform the test after the user has completed the required data entry. The test is preferably only completed after the user completes the required data entry. Applying force to open the hinged lid 104, or failing to complete data entry results in a failed or aborted test. Preferably, the users of the testing device 100 understand that the testing device 100 requires that all data entry be fulfilled and that the hinged lid 104 must remain closed to minimize failed or aborted tests.

At step 1320, a status of the test is shown to the user. The testing device 100 displays the status information to the user to confirm that the test is in process until the test is complete. Test information, whether prospective, in process or completed, is displayed on the LCD screen 110 in a fixed, text format that includes the test cartridge assembly 300 identifying information described above. Elements of the test record which are not yet completed are either left blank or displayed as "in progress" until the test is completed. Preferably, the user cannot perform other functions on the testing device 100 while a test is running. However, in other embodiments, the software may be altered to allow the user to perform other tasks on the testing device 100, such as reviewing a test log, while a test is being performed.

If during the test, it is determined that an appropriate light signal is detected by the sensor 206, the process proceeds to step 1322, where a positive result is reported, and the user is prompted to confirm. Once the user confirms, the user is prompted to re-enter the Lot/Location number at step 1324. If the Lot/Location number matches, the test data is logged and the process returns to the home screen of step 1306. If at step 1320, an appropriate light signal is not detected by the sensor 206, the process checks whether an appropriate light signal is detected for the negative control test. If so, the negative result is reported, as shown in the Negative Result screen 1500 of FIG. 15 and the user is prompted to remove the cartridge at step 1326. At this point, no RFID signal is detected and the test data is logged, with the process returning to the home screen of step 1306.

In addition, a test can be aborted by the software at any stage if, for example, the sensor 206, the motor 226, or any other hardware failure is detected or if the hinged lid 104 is opened. If at step 1320, such an issue is detected, a test error is reported at step 1328, and the user is prompted to remove the used test cartridge assembly 300. Once the test cartridge assembly 300 is removed, no RFID signal is detected by the RFID communications circuit 210, the error data is logged in ROM 1104, and the process returns to the home screen 1400 of step 1306. Similarly, the test can also be cancelled by the user at any stage until the test results are reported and stored. Aborted and cancelled tests are recorded in the test result file and stored in the flash ROM 1104 to prevent reuse of a previously used test cartridge assembly 300.

Test results are stored in the flash ROM 1104 in text form, preferably, as displayed on the touch screen LCD 110. Each test record preferably includes all of the above identified test information, including the identification of the test sample 414, the particular test performed, the date and time of the test, user ID and either a standard result or an identification that the test failed due to an error or was aborted.

All test results from either successfully completed or failed tests are stored in the flash ROM 1104. The user can recall the test results from the flash ROM 1104 to display on the touch screen LCD 110. Preferably, the flash ROM 1104 is large enough to store a substantial number of test records (e.g., five thousand records), preferably corresponding to the number of tests which could be expected to be performed in at least a week of testing by the testing device 100. It is contemplated that the user cannot delete records stored in the flash ROM 1104 in order to prevent unauthorized tampering with the test results. However, if the flash ROM 1104 is completely filled, the testing device 100 may automatically transition out of test mode and prompt the user to begin uploading data to a remotely located computer (not shown) via the interface ports 112. Once the upload is complete and the test records are deleted from the flash ROM 1104, the user may again perform tests using the testing device 100.

Conservation of battery power is an important concern which is addressed by the operating software at two levels. First, the current battery charge level is provided to the user on a periodic or continuous basis. The software also provides specific prompts to the user to initiate a recharging of the batteries 116 when the battery monitor circuit indicates that the batteries 116 charge level has fallen below a predetermined safe limit. Further, the software precludes the initiation of a new test when the battery charge level in the batteries 116 is too low for the safe completion of a test without risking a malfunction of the sensor 206, or other software or hardware function associated with the test function of the testing device 100.

Power supplied to the various peripheral devices, including the RFID communications circuit 210, the light sensing circuit 1200, the touch screen LCD 110 and the microprocessor 1102 is controlled by the operating system. Thus, supply of power may be selectively switched off when the functions of the various devices are not needed for current operation of the testing device 100. The entire testing device 100 may also be placed into a "power down" state upon receiving a user command, or after a predetermined period of inactivity of the testing device 100. The power down state differs from the complete absence of power in that the date/time clock continues to operate and the RAM 1106 is maintained on power from the batteries 116 instead of the recovery battery backup, which activates upon complete power absence from the battery pack.

However, when the power down occurs, nearly all software activity ceases except for the processes required to monitor the state of the touch screen LCD 110. The user may "power up" the unit by touching the touch screen LCD 110. As previously mentioned, upon detection of the restoration of batteries 116 power after a total power loss, the software does not require the entry of date and time information as the recovery battery backup maintains this minimal function. In the present embodiment, the time period set for the testing device 100 to automatically power down based on a period of inactivity depends on which menu is displayed. The delay periods are preferably adjustable using the settings menu of step 1312.

It will be appreciated by those of ordinary skill in the art that changes and modifications may be made to the embodiments described above without departing from the spirit and scope of the invention. Therefore, the present invention is not limited to the embodiments described above but is intended to cover all such modifications within the scope and spirit of the invention. It will be appreciated by those skilled in the art that alternative arrangements of the test cartridge assembly 300, including the combination of reservoir card 500 and test cartridge base 400 into a single subassembly, storing some of the necessary reagents 504, 506 on both the test cartridge base 400 and reservoir card 500, or direct sample deposition into the necessary reagents 504, 506 for performing the desired test, are all within the scope of this disclosure.

What is claimed:

1. A system for rapidly detecting the presence of an analyte in a biological sample, comprising:
   (a) a biosensor reagent including at least one antibody specific for a predetermined analyte and a bioluminescent agent, wherein the at least one antibody is expressed on the surface of living, engineered lymphocytes and wherein the bioluminescent agent is expressed by the living, engineered lymphocytes, the biosensor reagent being operative to:
      (i) detect the presence of a specific analyte in a sample to be tested, and
      (ii) emit a detectable light signal when the biosensor reagent reacts with the sample and detects the presence of the specific analyte in the sample;
   (b) a test cartridge, wherein the test cartridge further includes:
      (i) a reservoir card, wherein the reservoir card further includes the biosensor reagent;
      (ii) a test cartridge base, wherein the test cartridge base is configured to accept the reservoir card and wherein the test cartridge base further includes:
         a) a reaction chamber having a central axis, wherein the reaction chamber has the shape of a revolved half ellipse;
         b) an inlet channel connected to the reaction chamber, wherein the inlet channel is positioned above the reaction chamber at an angle of 15-60 degrees above the horizontal, and wherein the inlet channel is offset from the central axis of the reaction chamber; and
         c) wherein upon introducing the sample into the test cartridge base through the inlet channel, the sample is homogeneously mixed with the biosensor reagent while minimizing damage to the living, engineered lymphocytes and minimizing any bubbling of the mixed biosensor reagent and sample in the reaction chamber,
      (iii) wherein the reservoir card and the cartridge base further include fluid ports formed therein, and wherein the fluid ports are sealed prior to use or otherwise adapted to prevent cross-contamination of any fluids contained in the reservoir card or the test cartridge base; and (c) a testing unit adapted to receive the test cartridge, the testing unit including a sensor for detecting the detectable light signal emitted by the biosensor reagent upon reacting with the sample, the detection of the emitted detectable light signal being indicative of the presence of the analyte in the sample and, wherein detection of the specific analyte in the sample occurs in real time.

2. The system of claim 1, wherein the sensor is a photomultiplier tube having an active surface, and wherein the size of the active surface is optimized to reduce background noise and increase the signal to noise ratio of the emitted light detectable signal.

3. The system of claim 1, wherein the reservoir card is configured to be inserted into the test cartridge base and to be permanently retained therein by one or more retention features.

4. The system of claim 1, wherein the test cartridge base further comprises a fluid displacement mechanism, and wherein actuation of the fluid displacement mechanism causes the biosensor reagent stored in the reservoir card to be displaced into the reaction chamber.

5. The system of claim 1, wherein the testing unit further comprises a motor and piston assembly configured to actuate the fluid displacement mechanism.

6. The system of claim 1, wherein the testing unit is a portable testing unit.

7. The system of claim 1, further comprising at least one additive located in the reaction chamber, the at least one additive being operative to minimize the formation of bubbles in the test chamber during mixing of the biological sample and the biosensor reagent.

8. The system of claim 7, wherein the at least one additive includes a surfactant.

9. The system of claim 1, further comprising a disruptor for disrupting individual cells of an analyte in the biological sample prior to mixing the biological sample with the biosensor reagent.

10. The system of claim 9, wherein the disruptor is at least one of an enzyme operative to release O-antigens from the cell surface, a sonicator operative to fragment the cells, a French Press operative to fragment the cells, and a chemical treatment operative to release LPS from the cells of the analyte.

11. The system of claim 1, wherein the biosensor reagent is pre-charged with coelenterazine, and wherein any excess coelenterazine is removed from the biosensor reagent prior to reacting the biosensor reagent with the biological sample to be tested.

12. The system of claim 1, wherein the biological sample to be tested is derived from food including at least one of beef, poultry, pork and other meats, fish, and vegetable matter.

13. The system of claim 1, wherein real time is within the range of within about five minutes from combining the biological sample and the biosensor reagent.

14. The system of claim 1, further comprising a second control reagent operative to react with the biosensor reagent to determine a proper functioning of the testing unit, wherein the biosensor reagent reacts with the biological sample to be tested prior to the second control reagent reacting with the biosensor reagent.

15. A testing device for real time detection of an analyte in a biological sample, the testing device comprising:
(a) a housing comprising a lid and an input/output device;
(b) an analysis portion comprising:
(i) a recess in the housing for accepting a disposable test cartridge containing a biological sample to be tested, wherein the test cartridge includes:
a) a reservoir card, wherein the reservoir card further includes a biosensor reagent; and
b) a test cartridge base, wherein the test cartridge base is configured to accept the reservoir card and wherein the test cartridge base further includes:
i) a reaction chamber having a central axis, wherein the reaction chamber has the shape of a revolved half ellipse; and
ii) an inlet channel connected to the reaction chamber, wherein the inlet channel is positioned above the reaction chamber at an angle of 15-60 degrees above the horizontal, and wherein the inlet channel is offset from the central axis of the reaction chamber,
c) wherein the reservoir card and the cartridge base further include fluid ports formed therein, and wherein the fluid ports are sealed prior to use or otherwise adapted to prevent cross-contamination of any fluids contained in the reservoir card or the test cartridge base;
(ii) an actuator for interacting with the test cartridge when the lid is closed, the actuator causing the biosensor reagent in the test cartridge to be displaced to react with the biological sample during the performance of a test, the biosensor reagent including at least one antibody specific for a predetermined analyte and a bioluminescent agent; wherein the at least one antibody is expressed on the surface of living, engineered lymphocytes and wherein the bioluminescent agent is expressed by the living, engineered lymphocytes, and wherein upon introducing the biological sample into the test cartridge base through the inlet channel, the biological sample is homogeneously mixed with the biosensor reagent while minimizing damage to the living, engineered lymphocytes and minimizing any bubbling of the mixed biosensor reagent and biological sample in the reaction chamber; and
(iii) a sensor associated with the recess in the housing to detect a light signal emitted after the at least one biosensor reagent has been displaced by the actuator to react with the biological sample and to generate an output signal; and
(c) a control unit configured to:
(i) receive an input from a user by way of the input/output device to initiate a test;
(ii) in response to receiving the user input and after the biological sample has been deposited in the recess of the analysis portion, actuate the actuator to displace the biosensor reagent in the test cartridge to react with the biological sample;
(iii) receive the output signal from the sensor; and
(iv) output a test result to the user on the input/output device.

16. The testing device of claim 15, wherein the sensor is a photomultiplier tube having an active surface, and wherein the size of the active surface has been optimized to reduce background noise and increase the signal to noise ratio of the emitted signal.

17. The testing device of claim 16, further comprising an RFID communications circuit for receiving one or more signals from the test cartridge, wherein the one or more signals identify at least one of a test type to be run and whether the test cartridge was previously used.

18. The testing device of claim 16, wherein the biosensor reagent is pre-charged with coelenterazine, and wherein any excess coelenterazine is removed from the biosensor reagent prior to reacting the biosensor reagent with the sample to be tested.

19. The testing device of claim 16, further comprising a disruptor for disrupting individual cells of an analyte in the sample prior to mixing the sample with the biosensor reagent.

20. The testing device of claim 19, wherein the disruptor is at least one of an enzyme operative to release O-antigens from the cell surface, a sonicator operative to fragment the cells, a French Press operative to fragment the cells, and a chemical treatment operative to release LPS from the cells of the analyte.

21. The testing device of claim 16, wherein the testing device is a portable testing device.

\* \* \* \* \*